United States Patent [19]
Wertz et al.

[11] Patent Number: 5,789,229
[45] Date of Patent: *Aug. 4, 1998

[54] STRANDED RNA VIRUS PARTICLES

[75] Inventors: Gail W. Wertz; Qingzhong Yu; Laurence A. Ball; John N. Barr; Sean P. J. Whelan, all of Birmingham, Ala.

[73] Assignee: UAB Research Foundation, Birmingham, Ala.

[*] Notice: The term of this patent shall not extend beyond the expiration date of Pat. No. 5,716,821.

[21] Appl. No.: 514,975

[22] Filed: Sep. 29, 1995

Related U.S. Application Data

[63] Continuation-in-part of Ser. No. 475,587, Jun. 7, 1995, abandoned, which is a continuation-in-part of Ser. No. 316,438, Sep. 30, 1994, Pat. No. 5,716,821.

[51] Int. Cl.$^6$ ................................ C12N 7/00; C12N 7/01
[52] U.S. Cl. .................................. 435/235.1; 435/320.1; 435/172.3; 514/44
[58] Field of Search .................... 435/320.1, 240.2, 435/325, 235.1, 172.3; 424/93.1; 514/44

[56] References Cited

U.S. PATENT DOCUMENTS

| | | | |
|---|---|---|---|
| 4,122,167 | 10/1978 | Buynak et al. | 424/89 |
| 4,145,252 | 3/1979 | Buynak et al. | 195/1.3 |
| 5,149,650 | 9/1992 | Wertz et al. | 435/243 |
| 5,166,057 | 11/1992 | Palese et al. | 435/69.1 |
| 5,194,595 | 3/1993 | Wathen | 530/395 |
| 5,223,254 | 6/1993 | Paradiso et al. | 424/89 |
| 5,288,630 | 2/1994 | Wathen | 435/240.2 |

FOREIGN PATENT DOCUMENTS

| | | |
|---|---|---|
| WO 92/01471 | 2/1992 | WIPO . |
| WO 92/04375 | 3/1992 | WIPO . |
| WO 92/07940 | 5/1992 | WIPO . |
| WO 93/21310 | 10/1993 | WIPO . |

OTHER PUBLICATIONS

Holland, J. J. The Viruses: The Rhabdoviruses. Plenum Press, Wagner, R.R (Ed.). pp. 297–360 1987.

Fuerst, et al. Eukaryotic Transient-Expression System Based on Recombinant Vaccinia Virus that Synthesizes Bacteriophage T7 RNA polymerase. Proc. Natl. Acad. Sci., vol. 83, pp. 8122–8126 Nov. 1986.

Garcia-Sastre, A. and Palese, P., "Genetic Manipulation of Negative-Strand RNA Virus Genomes," *Annu. Rev. Microbiol.*, vol. 47, 765–790 (1993).

Palese,P., "Genetic Engineering of Infectious Negative-Strand RNA Viruses," *Trends in Microbiology*, vol. 3, No. 4, 123–125 (1995).

Pattnaik, A., et al., "The Termini of VSV DI Particle RNAs are Sufficient to Signal RNA Encapsidation, Replication, and Badding to Generate Infectious Particles," *Virology*, vol. 206, 760–764 (1995).

Rice, C., "Examples of Expression Systems Based on Animal RNA Viruses: Alphaviruses and Influenza Virus," *Current Opinion in Biotechnology*, vol. 3, 523–532 (1992).

Wertz, G.W. and Melero, J.A., "Workshop on 'Reverse Genetics of Negative Stranded RNA Viruses'Sponsored by the Juan March Institute, Madrid, Spain," *Virus Research*, vol. 30, 215–219 (1993).

Whelan, S., et al., "Efficient Recovery of Infectious Vesicular Stomatitis Virus Entirely from cDNA Clones," *Proc. Natl. Acad. Sci. USA*, vol. 92, 8388–8392 (1995).

Yamanaka, K., et al., "In Vivo Analysis of the Promoter Structure of the Influenza Virus RNA Genome Using a Transfection System with an Engineered RNA," *Proc. Natl. Acad. Sci. USA*, vol. 88, 5369–5373 (1991).

Yu, Q., et al., "Functional cDNA Clones of the Human Respiratory Syncytial (RS) Virus N, P, and L Proteins Support Replication of RS Virus Genomic RNA Analogs and Define Minimal trans-Acting Requirements for RNA Replication," *Journal of Virology*, 2412–2419 (1995).

Amann et al., "Bovine Respiratory Syncytial Virus Nucleocapsid Protein: mRNA Sequence Analysis and Expression from Recombinant Vaccinia Virus Vectors", *Journal of General Virology*, (1992), vol. 73, pp. 999–1003.

Bangham et al., "Human and Murine Cytotoxic T Cells Specific to Respiratory Syncytial Virus Recognize the Viral Nucleoprotein (N), but not the Major Glycoprotein (G), Expressed by Vaccinia Virus Recombinants", *Journal of Immunology*, (Dec. 1986), vol. 137, No. 12, pp. 3973–3977.

Cherrie et al., "Human Cytotoxic T Cells Stimulated by Antigen on Dendritic Cells Recognize the N, SH, F, M, 22K, and 1b proteins of Respiratory Syncytial Virus", *J. Virology*, (Apr. 1992), vol. 66, No. 4, pp. 2102–2110.

Collins and Wertz, "The 1A Protein Gene of Human Respiratory Synytial Virus: Nucleotide Sequence of the mRNA and a Related Polycistronic Transcript", *Virology*(1985), vol. 141, pp. 283–291.

Collins and Wertz, "cDNA Cloning and Transcriptional Mapping of Nine Polyadenylylated RNAs Encoded by the Genome of Human Respiratory Syncytial Virus", *Proc. Natl. Acad. SCi. USA*, (Jun. 1983), vol. 80, pp. 3208–3212.

Collins and Wertz, "The Envelope-Associated 22K Protein of the Human Respiratory Syncytial Virus: Nucleotide Sequences of the mRNA and a Related Polytranscript", *J. Virology*, (Apr. 1985), vol. 54, No. 1, pp. 65–71.

(List continued on next page.)

*Primary Examiner*—Jasemine C. Chambers
*Assistant Examiner*—Deborah J. R. Clark
*Attorney, Agent, or Firm*—Benjamin Aaron Adler

[57] ABSTRACT

Recombinant methods for recovering wildtype or engineered negative stranded, non-segmented RNA virus genomes containing non-coding 3' and 5' regions (e.g. leader or trailer regions) surrounding one, several or all of the genes of the virus or one or more heterologous gene(s) in the form of ribonucleocapsids containing N, P and L proteins, which are capable of replicating and assembling with the remaining structural proteins to bud and form virions, or which are only capable of infecting one cell, or are transcribing particles, are disclosed. Novel vaccines, gene therapy vectors and antiviral compounds based on these viral particles are also disclosed.

15 Claims, 7 Drawing Sheets

OTHER PUBLICATIONS

Collins and Wertz, "Nucleotide Sequences of the 1B and 1C Nonstructural Protein mRNAs of Human Respiratory Syncytial Virus", *Virology*, (1985), vol. 143, pp. 442–451.

Collins et al., "Correct Sequence for the Major Nucleocapsid Protein mRNA of Respiratory Syncytial Virus", *Virology*(1985), vol. 146, pp. 69–77.

Collins et al., "Indentification of a Tenth mRNA of Respiratory Syncytial Virus and Assignment of Polpeptides to the 10 Viral Genes", *J. Virology*, (Feb. 1984), vol. 49, No. 2, pp. 572–578.

Collins et al., "Nucleotide Sequence of the Gene Encoding the Fusion (F) Glycoprotein of Human Respiratory Syncytial Virus", *Proc. Natl. Acad. Sci. USA*, (Dec. 1984), vol. 81, pp. 7683–7687.

Collins et al., "Rescue of a 7502–Nucleotide (49.3% of Full–Length) Synthetic Analog of Respiratory Syncytial Virus Genomic RNA", *Virology*, (1993), vol. 195, pp. 252–256.

Collins et al., "Rescue of Synthetic Analogs of Respiratory Syncytial Virus Genomic RNA and Effect of Truncations and Mutations on the Expression of a Foreign Reporter Gene", *Proc. Natl. Acad. Sci. USA*, (Nov. 1991), vol. 88, pp. 9663–9667.

Dickens et al., "Transcriptional Mapping of Human Respiratory Syncytial Virus", *J. Virology*, (Nov. 1984), vol. 52, No. 2, pp. 364–369.

Huang et al., "Characterization of the 10 Proteins of Human Respiratory Syncytial Virus: Identification of a Fourth Envelope–Associated Protein", *Virus Research*, (1985), vol. 2, pp. 157–173 (Abstract Only).

King et al., "Recombinant Vaccinia Viruses Carrying the N Gene of Human Respiratory Syncytial Virus: Studies of Gene Expression in Cell Culture and Immune Response in Mice", *J. Virology*, (Sep. 1987), vol. 61, No. 9, pp. 2885–2890.

Lawson et al., "Recombinant vesicular stomatitis viruses from DNA", *Proc. Natl. Acad. Sci. USA*, (May 1995), vol. 92, pp. 4477–4481.

Lerch et al., "Characterization of Bovine Respiratory Syncytial Virus Proteins and mRNAs and Generation of cDNA Clones to the Viral mRNAs", *J. Virology*, (Feb. 1989), vol. 631, pp. 833–840.

Lerch et al., "Nucleotide Sequence Analysis and Expression from Recombinant Vectors Demonstrate that the Attachment Protein G of Bovine Respiratory Syncytial Virus is Distinct from that of Human Respiratory Syncytial Virus", *J. Virology*, (Nov. 1990), vol. 64, No. 11, pp. 5559–5569.

Mink et al., "Nucleotide Sequences of the 3'Leader and 5'Trailer Regions of Human Respiratory Syncytial Virus Genomic RNA", *Virology*(1991), vol. 185, pp. 615–624.

Openshaw et al., "Helper T Cell Recognition of Respiratory Syncytial Virus in Mice", *J. Gen. Virol.* (1988), vol. 69, pp. 305, 312.

Pattnaik et al., "Cells that Express all Five Proteins of Vesicular Stomatitis Virus from Cloned cDNAs Support Replication, Assembly and Budding of Defective Interfering Prticles", *Proc. Natl. Acad. Sci. USA*, (Feb. 1991), vol. 88, pp. 1379–1383.

Pattnaik et al., "Infectious Defective Interfering Particles of VSV from Transcripts of a cDNA Clone", *Cell*, (Jun. 12, 1992), vol. 69, pp. 1011–1020.

Pattnaik et al., "Replication and Amplification of Defective Interfering Particle RNAs of Vesicular Stomatitis Virus in Cells Expressing Viral Proteins from Vectors Containing Cloned cDNAs", *J. Virology*, (Jun. 1990), vol. 64, pp. 2948–2957.

Pemberton et al., "Cytotoxic T Cell Specificity for Respiratory Syncytial Virus Proteins: Fusion Protein is an Important Target Antigen", *J. Gen. Virol.*, (1987), vol. 68, pp. 2177–2182.

Satake and Venkatesan, "Nucleotide Sequence of the Gene Encoding Respiratory Syncytial Virus Genomic RNA Matrix Protein", *J. Virology*, (Apr. 1984), vol. 50, No. 1, pp. 92–99.

Satke et al., "Sequence Analysis of the Respiratory Syncytial Virus Phosphoprotein Gene", *J. Virology*(Dec.1984), vol. 52, No. 3, pp. 991–994.

Schnell et al., "Infectious rabies viruses from cloned cDNA" *EMBO J.*, (1994), vol. 13, pp. 4195–4203.

Stec et al., "Sequence Analysis of the Polymerase L Gene of Human Respiratory Syncytial Virus and Predicted Phylogency of Nonsegmented Negative–Strand Viruses", *Virology*, (1991), vol. 183, pp. 273–287.

Stott et al., "Human Respiratory Syncytial Virus Glycoprotein G Expressed from a Recombinant Vaccinia Virus Protects Mice against Liv–Virus Challenge", *J. Virology*, (Nov. 1986), vol. 60, No. 2, pp. 607–613.

Stott et al., "Immune and Histopathological Responses in Animals Vaccinated with Recombinant Vaccinia Viruses that Express Individual Genes of Human Respiratory Syncytial Virus", *J. Virology*, (Dec. 1987), vol. 61, No. 12, pp. 3855–3861.

Sullender et al., "Genetic Diversity of the Attachment Protein of Subgroup B Respiratory Syncytial Viruses", *J. Virology*, (Oct. 1991), vol. 65, No. 10, pp. 5425–5434.

Sullender et al., "The Respiratory Syncytial Virus Subgroup B Attachment Glycoprotein: Analysis of Sequence, Expression from a Recombinasnt Vector, and Evaluation as an Immunogen against Homologous and Heterologous Subgrroup Virus Cahllenge", *Virology*, (1990), vol. 178, pp. 195–203.

Wertz et al., "Expression of the Fusion Protein of Human Respiratory Syncytial Virus from Recombinant Vaccinia Virus Vectors and Protection of Vaccinated Mice", *J. Virology*, (Feb. 1987), vol. 61, No. 2, pp. 293–301.

Wertz et al., "Nucleotide Sequence of the G Protein Gene of Human Respiratory Syncytial Virus Reveals an Unusual Type of Viral Membrane Protein", *Proc. Natl. Acad. Sci. USA*, (Jun. 1985), vol. 82, pp. 4075–4079.

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 6578 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 9..6504

( x i ) SEQUENCE DESCRIPTION: SEQ ID NO:1:

```
GGGACAAAAT GGATCCCATT ATTAATGGAA ATTCTGCTAA TGTTTATCTA ACCGATGGTT     60
ATTTAAAAGG TGTTATCTCT TTCTCAGAGT GTAATGCTTT AGGAAGTTAC ATATTCAATG    120
GTCCTTATCT CAAAAATGAT TATACCAACT TAATTAGTAG ACAAAATCCA TTAATAGAAC    180
ACATGAATCT AAAGAAACTA AATATAACAC AGTCCTTAAT ATCTAAGTAT CATAAAGGTG    240
AAATAAAATT AGAAGAACCT ACTTATTTTC AGTCATTACT TATGACATAC AAGAGTATGA    300
CCTCGTCAGA ACAGATTGCT ACCACTAATT TACTTAAAAA GATAATAAGA AGAGCTATAG    360
AAATAAGTGA TGTCAAAGTC TATGCTATAT TGAATAAACT AGGGCTTAAA GAAAAGGACA    420
AGATTAAATC CAACAATGGA CAAGATGAAG ACAACTCAGT TATTACGACC ATAATCAAAG    480
ATGATATACT TTCAGCTGTT AAAGATAATC AATCTCATCT TAAAGCAGAC AAAAATCACT    540
CTACAAAACA AAAAGACACA ATCAAAACAA CACTCTTGAA GAAATTGATG TGTTCAATGC    600
AACATCCTCC ATCATGGTTA ATACATTGGT TTAACTTATA CACAAAATTA AACAACATAT    660
TAACACAGTA TCGATCAAAT GAGGTAAAAA ACCATGGGTT TACATTGATA GATAATCAAA    720
CTCTTAGTGG ATTTCAATTT ATTTTGAACC AATATGGTTG TATAGTTTAT CATAAGGAAC    780
TCAAAAGAAT TACTGTGACA ACCTATAATC AATTCTTGAC ATGGAAAGAT ATTAGCCTTA    840
GTAGATTAAA TGTTTGTTTA ATTACATGGA TTAGTAACTG CTTGAACACA TTAAATAAAA    900
GCTTAGGCTT AAGATGCGGA TTCAATAATG TTATCTTGAC ACAACTATTC CTTTATGGAG    960
ATTGTATACT AAAGCTATTT CACAATGAGG GGTTCTACAT AATAAAAGAG GTAGAGGGAT   1020
TTATTATGTC TCTAATTTTA AATATAACAG AAGAAGATCA ATTCAGAAAA CGATTTTATA   1080
ATAGTATGCT CAACAACATC ACAGATGCTG CTAATAAAGC TCAGAAAAAT CTGCTATCAA   1140
GAGTATGTCA TACATTATTA GATAAGACAG TGTCCGATAA TATAATAAAT GGCAGATGGA   1200
TAATTCTATT AAGTAAGTTC CTTAAATTAA TTAAGCTTGC AGGTGACAAT AACCTTAACA   1260
ATCTGAGTGA ACTATATTTT TTGTTCAGAA TATTTGGACA CCCAATGGTA GATGAAAGAC   1320
```

| | | | | | | |
|---|---|---|---|---|---|---|
| AAGCCATGGA | TGCTGTTAAA | ATTAATTGCA | ATGAGACCAA | ATTTTACTTG | TTAAGCAGTC | 1380 |
| TGAGTATGTT | AAGAGGTGCC | TTTATATATA | GAATTATAAA | AGGGTTTGTA | AATAATTACA | 1440 |
| ACAGATGGCC | TACTTTAAGA | AATGCTATTG | TTTTACCCTT | AAGATGGTTA | ACTTACTATA | 1500 |
| AACTAAACAC | TTATCCTTCT | TTGTTGGAAC | TTACAGAAAG | AGATTTGATT | GTGTTATCAG | 1560 |
| GACTACGTTT | CTATCGTGAG | TTTCGGTTGC | CTAAAAAGT | GGATCTTGAA | ATGATTATAA | 1620 |
| ATGATAAAGC | TATATCACCT | CCTAAAAATT | TGATATGGAC | TAGTTTCCCT | AGAAATTACA | 1680 |
| TGCCATCACA | CATACAAAAC | TATATAGAAC | ATGAAAAATT | AAAATTTTCC | GAGAGTGATA | 1740 |
| AATCAAGAAG | AGTATTAGAG | TATTATTTAA | GAGATAACAA | ATTCAATGAA | TGTGATTTAT | 1800 |
| ACAACTGTGT | AGTTAATCAA | AGTTATCTCA | ACAACCCTAA | TCATGTGGTA | TCATTGACAG | 1860 |
| GCAAAGAAAG | AGAACTCAGT | GTAGGTAGAA | TGTTTGCAAT | GCAACCGGGA | ATGTTCAGAC | 1920 |
| AGGTTCAAAT | ATTGGCAGAG | AAAATGATAG | CTGAAAACAT | TTTACAATTC | TTTCCTGAAA | 1980 |
| GTCTTACAAG | ATATGGTGAT | CTAGAACTAC | AAAAAATATT | AGAATTGAAA | GCAGGAATAA | 2040 |
| GTAACAAATC | AAATCGCTAC | AATGATAATT | ACAACAATTA | CATTAGTAAG | TGCTCTATCA | 2100 |
| TCACAGATCT | CAGCAAATTC | AATCAAGCAT | TTCGATATGA | AACGTCATGT | ATTTGTAGTG | 2160 |
| ATGTGCTGGA | TGAACTGCAT | GGTGTACAAT | CTCTATTTTC | CTGGTTACAT | TTAACTATTC | 2220 |
| CTCATGTCAC | AATAATATGC | ACATATAGGC | ATGCACCCCC | CTATATAGGA | GATCATATTG | 2280 |
| TAGATCTTAA | CAATGTAGAT | GAACAAAGTG | GATTATATAG | ATATCACATG | GGTGGCATCG | 2340 |
| AAGGGTGGTG | TCAAAAACTA | TGGACCATAG | AAGCTATATC | ACTATTGGAT | CTAATATCTC | 2400 |
| TCAAAGGGAA | ATTCTCAATT | ACTGCTTTAA | TTAATGGTGA | CAATCAATCA | ATAGATATAA | 2460 |
| GCAAACCAAT | CAGACTCATG | GAAGGTCAAA | CTCATGCTCA | AGCAGATTAT | TTGCTAGCAT | 2520 |
| TAAATAGCCT | TAAATTACTG | TATAAAGAGT | ATGCAGGCAT | AGGCCACAAA | TTAAAAGGAA | 2580 |
| CTGAGACTTA | TATATCACGA | GATATGCAAT | TTATGAGTAA | AACAATTCAA | CATAACGGTG | 2640 |
| TATATTACCC | AGCTAGTATA | AAGAAAGTCC | TAAGAGTGGG | ACCGTGGATA | AACACTATAC | 2700 |
| TTGATGATTT | CAAAGTGAGT | CTAGAATCTA | TAGGTAGTTT | GACACAAGAA | TTAGAATATA | 2760 |
| GAGGTGAAAG | TCTATTATGC | AGTTTAATAT | TTAGAAATGT | ATGGTTATAT | AATCAGATTG | 2820 |
| CTCTACAATT | AAAAAATCAT | GCATTATGTA | ACAATAAACT | ATATTGGAC | ATATTAAAGG | 2880 |
| TTCTGAAACA | CTTAAAAACC | TTTTTAATC | TTGATAATAT | TGATACAGCA | TTAACATTGT | 2940 |
| ATATGAATTT | ACCCATGTTA | TTTGGTGGTG | GTGATCCCAA | CTTGTTATAT | CGAAGTTTCT | 3000 |
| ATAGAAGAAC | TCCTGACTTC | CTCACAGAGG | CTATAGTTCA | CTCTGTGTTC | ATACTTAGTT | 3060 |
| ATTATACAAA | CCATGACTTA | AAAGATAAAC | TTCAAGATCT | GTCAGATGAT | AGATTGAATA | 3120 |
| AGTTCTTAAC | ATGCATAATC | ACGTTGACA | AAGACCCTAA | TGCTGAATTC | GTAACATTGA | 3180 |
| TGAGAGATCC | TCAAGCTTTA | GGGTCTGAGA | GACAAGCTAA | AATTACTAGC | GAAATCAATA | 3240 |
| GACTGGCAGT | TACAGAGGTT | TTGAGTACAG | CTCCAAACAA | AATATTCTCC | AAAAGTGCAC | 3300 |
| AACATTATAC | TACTACAGAG | ATAGATCTAA | ATGATATTAT | GCAAAATATA | GAACCTACAT | 3360 |
| ATCCTCATGG | GCTAAGAGTT | GTTTATGAAA | GTTTACCCTT | TTATAAAGCA | GAGAAAATAG | 3420 |
| TAAATCTTAT | ATCAGGTACA | AAATCTATAA | CTAACATACT | GGAAAAAACT | TCTGCCATAG | 3480 |
| ACTTAACAGA | TATTGATAGA | GCCACTGAGA | TGATGAGGAA | AACATAACT | TTGCTTATAA | 3540 |
| GGATACTTCC | ATTGGATTGT | AACAGAGATA | AAGAGAGAT | ATTGAGTATG | GAAAACCTAA | 3600 |
| GTATTACTGA | ATTAAGCAAA | TATGTTAGGG | AAAGATCTTG | GTCTTTATCC | AATATAGTTG | 3660 |
| GTGTTACATC | ACCCAGTATC | ATGTATACAA | TGGACATCAA | ATATACTACA | AGCACTATAT | 3720 |

```
CTAGTGGCAT AATTATAGAG AAATATAATG TTAACAGTTT AACACGTGGT GAGAGAGGAC    3780
CCACTAAACC ATGGGTTGGT TCATCTACAC AAGAGAAAAA AACAATGCCA GTTTATAATA    3840
GACAAGTCTT AACCAAAAAA CAGAGAGATC AAATAGATCT ATTAGCAAAA TTGGATTGGG    3900
TGTATGCATC TATAGATAAC AAGGATGAAT TCATGGAAGA ACTCAGCATA GGAACCCTTG    3960
GGTTAACATA TGAAAAGGCC AAGAAATTAT TTCCACAATA TTTAAGTGTC AATTATTTGC    4020
ATCGCCTTAC AGTCAGTAGT AGACCATGTG AATTCCCTGC ATCAATACCA GCTTATAGAA    4080
CAACAAATTA TCACTTTGAC ACTAGCCCTA TTAATCGCAT ATTAACAGAA AAGTATGGTG    4140
ATGAAGATAT TGACATAGTA TTCCAAAACT GTATAAGCTT TGGCCTTAGT TTAATGTCAG    4200
TAGTAGAACA ATTTACTAAT GTATGTCCTA ACAGAATTAT TCTCATACCT AAGCTTAATG    4260
AGATACATTT GATGAAACCT CCCATATTCA CAGGTGATGT TGATATTCAC AAGTTAAAAC    4320
AAGTGATACA AAAACAGCAT ATGTTTTTAC CAGACAAAAT AAGTTTGACT CAATATGTGG    4380
AATTATTCTT AAGTAATAAA ACACTCAAAT CTGGATCTCA TGTTAATTCT AATTTAATAT    4440
TGGCACATAA AATATCTGAC TATTTTCATA ATACTTACAT TTAAGTACT AATTTAGCTG    4500
GACATTGGAT TCTGATTATA CAACTTATGA AAGATTCTAA AGGTATTTTT GAAAAGATT    4560
GGGGAGAGGG ATATATAACT GATCATATGT TTATTAATTT GAAAGTTTTC TTCAATGCTT    4620
ATAAGACCTA TCTCTTGTGT TTTCATAAAG GTTATGGCAA AGCAAAGCTG GAGTGTGATA    4680
TGAACACTTC AGATCTTCTA TGTGTATTGG AATTAATAGA CAGTAGTTAT GGAAGTCTA    4740
TGTCTAAGGT ATTTTTAGAA CAAAAAGTTA TCAAATACAT TCTTAGCCAA GATGCAAGTT    4800
TACATAGAGT AAAAGGATGT CATAGCTTCA AATTATGGTT TCTTAAACGT CTTAATGTAG    4860
CAGAATTCAC AGTTTGCCCT TGGGTTGTTA ACATAGATTA TCATCCAACA CATATGAAAG    4920
CAATATTAAC TTATATAGAT CTTGTTAGAA TGGGATTGAT AAATATAGAT AGAATACACA    4980
TTAAAAATAA ACACAAATTC AATGATGAAT TTTATACTTC TAATCTCTTC TACATTAATT    5040
ATAACTTCTC AGATAATACT CATCTATTAA CTAAACATAT AAGGATTGCT AATTCTGAAT    5100
TAGAAAATAA TTACAACAAA TTATATCATC CTACACCAGA AACCCTAGAG AATATACTAG    5160
CCAATCCGAT TAAAAGTAAT GACAAAAAGA CACTGAATGA CTATTGTATA GGTAAAAATG    5220
TTGACTCAAT AATGTTACCA TTGTTATCTA ATAAGAAGCT TATTAAATCG TCTGCAATGA    5280
TTAGAACCAA TTACAGCAAA CAAGATTTGT ATAATTTATT CCCTATGGTT GTGATTGATA    5340
GAATTATAGA TCATTCAGGC AATACAGCCA AATCCAACCA ACTTTACACT ACTACTTCCC    5400
ACCAAATATC TTTAGTGCAC AATAGCACAT CACTTTACTG CATGCTTCCT TGGCATCATA    5460
TTAATAGATT CAATTTTGTA TTTAGTTCTA CAGGTTGTAA AATTAGTATA GAGTATATTT    5520
TAAAAGATCT TAAAATTAAA GATCCCAATT GTATAGCATT CATAGGTGAA GGAGCAGGGA    5580
ATTTATTATT GCGTACAGTA GTGGAACTTC ATCCTGACAT AAGATATATT TACAGAAGTC    5640
TGAAAGATTG CAATGATCAT AGTTTACCTA TTGAGTTTTT AAGGCTGTAC AATGGACATA    5700
TCAACATTGA TTATGGTGAA AATTTGACCA TTCCTGCTAC AGATGCAACC AACAACATTC    5760
ATTGGTCTTA TTTACATATA AAGTTTGCTG AACCTATCAG TCTTTTTGTC TGTGATGCCG    5820
AATTGTCTGT AACAGTCAAC TGGAGTAAAA TTATAATAGA ATGGAGCAAG CATGTAAGAA    5880
AGTGCAAGTA CTGTTCCTCA GTTAATAAAT GTATGTTAAT AGTAAAATAT CATGCTCAAG    5940
ATGATATTGA TTTCAAATTA GACAATATAA CTATATTAAA AACTTATGTA TGCTTAGGCA    6000
GTAAGTTAAA GGGATCGGAG GTTTACTTAG TCCTTACAAT AGGTCCTGCG AATATATTCC    6060
CAGTATTTAA TGTAGTACAA AATGCTAAAT TGATACTATC AAGAACCAAA AATTTCATCA    6120
```

-continued

```
TGCCTAAGAA AGCTGATAAA GAGTCTATTG ATGCAAATAT TAAAAGTTTG ATACCCTTTC      6180

TTTGTTACCC TATAACAAAA AAAGGAATTA ATACTGCATT GTCAAAACTA AAGAGTGTTG      6240

TTAGTGGAGA TATACTATCA TATTCTATAG CTGGACGTAA TGAAGTTTTC AGCAATAAAC      6300

TTATAAATCA TAAGCATATG AACATCTTAA AATGGTTCAA TCATGTTTTA AATTTCAGAT      6360

CAACAGAACT AAACTATAAC CATTTATATA TGGTAGAATC TACATATCCT TACCTAAGTG      6420

AATTGTTAAA CAGCTTGACA ACCAATGAAC TTAAAAAACT GATTAAAATC ACAGGTAGTC      6480

TGTTATACAA CTTTCATAAT GAATAATGAA TAAAGATCTT ATAATAAAAA TTCCCATAGC      6540

TATACACTAA CACTGTATTC AATTATAGTT ATTAAAAA                              6578
```

(2) INFORMATION FOR SEQ ID NO:2:

(i) SEQUENCE CHARACTERISTICS:
        (A) LENGTH: 2165 amino acids
        (B) TYPE: amino acid
        (D) TOPOLOGY: linear (ii) MOLECULE TYPE: protein (xi) SEQUENCE DESCRIPTION: SEQ ID NO:2:

```
Met Asp Pro Ile Ile Asn Gly Asn Ser Ala Asn Val Tyr Leu Thr Asp
 1               5                  10                  15

Gly Tyr Leu Lys Gly Val Ile Ser Phe Ser Glu Cys Asn Ala Leu Gly
                20                  25                  30

Ser Tyr Ile Phe Asn Gly Pro Tyr Leu Lys Asn Asp Tyr Thr Asn Leu
            35                  40                  45

Ile Ser Arg Gln Asn Pro Leu Ile Glu His Met Asn Leu Lys Lys Leu
        50                  55                  60

Asn Ile Thr Gln Ser Leu Ile Ser Lys Tyr His Lys Gly Glu Ile Lys
 65                 70                  75                  80

Leu Glu Glu Pro Thr Tyr Phe Gln Ser Leu Leu Met Thr Tyr Lys Ser
                85                  90                  95

Met Thr Ser Ser Glu Gln Ile Ala Thr Thr Asn Leu Leu Lys Lys Ile
               100                 105                 110

Ile Arg Arg Ala Ile Glu Ile Ser Asp Val Lys Val Tyr Ala Ile Leu
           115                 120                 125

Asn Lys Leu Gly Leu Lys Glu Lys Asp Lys Ile Lys Ser Asn Asn Gly
       130                 135                 140

Gln Asp Glu Asp Asn Ser Val Ile Thr Thr Ile Ile Lys Asp Asp Ile
145                 150                 155                 160

Leu Ser Ala Val Lys Asp Asn Gln Ser His Leu Lys Ala Asp Lys Asn
                165                 170                 175

His Ser Thr Lys Gln Lys Asp Thr Ile Lys Thr Thr Leu Leu Lys Lys
            180                 185                 190

Leu Met Cys Ser Met Gln His Pro Pro Ser Trp Leu Ile His Trp Phe
        195                 200                 205

Asn Leu Tyr Thr Lys Leu Asn Asn Ile Leu Thr Gln Tyr Arg Ser Asn
    210                 215                 220

Glu Val Lys Asn His Gly Phe Thr Leu Ile Asp Asn Gln Thr Leu Ser
225                 230                 235                 240

Gly Phe Gln Phe Ile Leu Asn Gln Tyr Gly Cys Ile Val Tyr His Lys
                245                 250                 255

Glu Leu Lys Arg Ile Thr Val Thr Thr Tyr Asn Gln Phe Leu Thr Trp
            260                 265                 270
```

```
Lys Asp Ile Ser Leu Ser Arg Leu Asn Val Cys Leu Ile Thr Trp Ile
        275                 280                 285
Ser Asn Cys Leu Asn Thr Leu Asn Lys Ser Leu Gly Leu Arg Cys Gly
        290                 295                 300
Phe Asn Asn Val Ile Leu Thr Gln Leu Phe Leu Tyr Gly Asp Cys Ile
305                 310                 315                 320
Leu Lys Leu Phe His Asn Glu Gly Phe Tyr Ile Ile Lys Glu Val Glu
                    325                 330                 335
Gly Phe Ile Met Ser Leu Ile Leu Asn Ile Thr Glu Glu Asp Gln Phe
                340                 345                 350
Arg Lys Arg Phe Tyr Asn Ser Met Leu Asn Asn Ile Thr Asp Ala Ala
            355                 360                 365
Asn Lys Ala Gln Lys Asn Leu Leu Ser Arg Val Cys His Thr Leu Leu
        370                 375                 380
Asp Lys Thr Val Ser Asp Asn Ile Ile Asn Gly Arg Trp Ile Ile Leu
385                 390                 395                 400
Leu Ser Lys Phe Leu Lys Leu Ile Lys Leu Ala Gly Asp Asn Asn Leu
                405                 410                 415
Asn Asn Leu Ser Glu Leu Tyr Phe Leu Phe Arg Ile Phe Gly His Pro
            420                 425                 430
Met Val Asp Glu Arg Gln Ala Met Asp Ala Val Lys Ile Asn Cys Asn
        435                 440                 445
Glu Thr Lys Phe Tyr Leu Leu Ser Ser Leu Ser Met Leu Arg Gly Ala
        450                 455                 460
Phe Ile Tyr Arg Ile Ile Lys Gly Phe Val Asn Asn Tyr Asn Arg Trp
465                 470                 475                 480
Pro Thr Leu Arg Asn Ala Ile Val Leu Pro Leu Arg Trp Leu Thr Tyr
                485                 490                 495
Tyr Lys Leu Asn Thr Tyr Pro Ser Leu Leu Glu Leu Thr Glu Arg Asp
            500                 505                 510
Leu Ile Val Leu Ser Gly Leu Arg Phe Tyr Arg Glu Phe Arg Leu Pro
        515                 520                 525
Lys Lys Val Asp Leu Glu Met Ile Ile Asn Asp Lys Ala Ile Ser Pro
        530                 535                 540
Pro Lys Asn Leu Ile Trp Thr Ser Phe Pro Arg Asn Tyr Met Pro Ser
545                 550                 555                 560
His Ile Gln Asn Tyr Ile Glu His Glu Lys Leu Lys Phe Ser Glu Ser
                565                 570                 575
Asp Lys Ser Arg Arg Val Leu Glu Tyr Tyr Leu Arg Asp Asn Lys Phe
            580                 585                 590
Asn Glu Cys Asp Leu Tyr Asn Cys Val Val Asn Gln Ser Tyr Leu Asn
        595                 600                 605
Asn Pro Asn His Val Val Ser Leu Thr Gly Lys Glu Arg Glu Leu Ser
610                 615                 620
Val Gly Arg Met Phe Ala Met Gln Pro Gly Met Phe Arg Gln Val Gln
625                 630                 635                 640
Ile Leu Ala Glu Lys Met Ile Ala Glu Asn Ile Leu Gln Phe Phe Pro
                645                 650                 655
Glu Ser Leu Thr Arg Tyr Gly Asp Leu Glu Leu Gln Lys Ile Leu Glu
            660                 665                 670
Leu Lys Ala Gly Ile Ser Asn Lys Ser Asn Arg Tyr Asn Asp Asn Tyr
        675                 680                 685
Asn Asn Tyr Ile Ser Lys Cys Ser Ile Ile Thr Asp Leu Ser Lys Phe
690                 695                 700
```

-continued

| | | | | | | | | | | | | | | |
|---|---|---|---|---|---|---|---|---|---|---|---|---|---|---|
| Asn | Gln | Ala | Phe | Arg | Tyr | Glu | Thr | Ser | Cys | Ile | Cys | Ser | Asp | Val | Leu |
| 705 | | | | 710 | | | | | 715 | | | | | 720 |
| Asp | Glu | Leu | His | Gly | Val | Gln | Ser | Leu | Phe | Ser | Trp | Leu | His | Leu | Thr |
| | | | | 725 | | | | | 730 | | | | | 735 |
| Ile | Pro | His | Val | Thr | Ile | Ile | Cys | Thr | Tyr | Arg | His | Ala | Pro | Pro | Tyr |
| | | | | 740 | | | | 745 | | | | | 750 |
| Ile | Gly | Asp | His | Ile | Val | Asp | Leu | Asn | Asn | Val | Asp | Glu | Gln | Ser | Gly |
| | | | 755 | | | | 760 | | | | | 765 |
| Leu | Tyr | Arg | Tyr | His | Met | Gly | Ile | Glu | Gly | Trp | Cys | Gln | Lys | Leu |
| | 770 | | | | | 775 | | | | | 780 |
| Trp | Thr | Ile | Glu | Ala | Ile | Ser | Leu | Leu | Asp | Leu | Ile | Ser | Leu | Lys | Gly |
| 785 | | | | 790 | | | | | 795 | | | | | 800 |
| Lys | Phe | Ser | Ile | Thr | Ala | Leu | Ile | Asn | Gly | Asp | Asn | Gln | Ser | Ile | Asp |
| | | | | 805 | | | | | 810 | | | | | 815 |
| Ile | Ser | Lys | Pro | Ile | Arg | Leu | Met | Glu | Gly | Gln | Thr | His | Ala | Gln | Ala |
| | | | 820 | | | | | 825 | | | | | 830 |
| Asp | Tyr | Leu | Leu | Ala | Leu | Asn | Ser | Leu | Lys | Leu | Leu | Tyr | Lys | Glu | Tyr |
| | | | 835 | | | | 840 | | | | | 845 |
| Ala | Gly | Ile | Gly | His | Lys | Leu | Lys | Gly | Thr | Glu | Thr | Tyr | Ile | Ser | Arg |
| | 850 | | | | | 855 | | | | 860 |
| Asp | Met | Gln | Phe | Met | Ser | Lys | Thr | Ile | Gln | His | Asn | Gly | Val | Tyr | Tyr |
| 865 | | | | | 870 | | | | | 875 | | | | | 880 |
| Pro | Ala | Ser | Ile | Lys | Lys | Val | Leu | Arg | Val | Gly | Pro | Trp | Ile | Asn | Thr |
| | | | | 885 | | | | 890 | | | | | 895 |
| Ile | Leu | Asp | Asp | Phe | Lys | Val | Ser | Leu | Glu | Ser | Ile | Gly | Ser | Leu | Thr |
| | | | 900 | | | | | 905 | | | | | 910 |
| Gln | Glu | Leu | Glu | Tyr | Arg | Gly | Glu | Ser | Leu | Leu | Cys | Ser | Leu | Ile | Phe |
| | | 915 | | | | 920 | | | | | 925 |
| Arg | Asn | Val | Trp | Leu | Tyr | Asn | Gln | Ile | Ala | Leu | Gln | Leu | Lys | Asn | His |
| | 930 | | | | | 935 | | | | | 940 |
| Ala | Leu | Cys | Asn | Asn | Lys | Leu | Tyr | Leu | Asp | Ile | Leu | Lys | Val | Leu | Lys |
| 945 | | | | | 950 | | | | | 955 | | | | | 960 |
| His | Leu | Lys | Thr | Phe | Phe | Asn | Leu | Asp | Asn | Ile | Asp | Thr | Ala | Leu | Thr |
| | | | | 965 | | | | | 970 | | | | | 975 |
| Leu | Tyr | Met | Asn | Leu | Pro | Met | Leu | Phe | Gly | Gly | Gly | Asp | Pro | Asn | Leu |
| | | | 980 | | | | | 985 | | | | | 990 |
| Leu | Tyr | Arg | Ser | Phe | Tyr | Arg | Arg | Thr | Pro | Asp | Phe | Leu | Thr | Glu | Ala |
| | | 995 | | | | 1000 | | | | | 1005 |
| Ile | Val | His | Ser | Val | Phe | Ile | Leu | Ser | Tyr | Tyr | Thr | Asn | His | Asp | Leu |
| | | 1010 | | | | 1015 | | | | | 1020 |
| Lys | Asp | Lys | Leu | Gln | Asp | Leu | Ser | Asp | Asp | Arg | Leu | Asn | Lys | Phe | Leu |
| 1025 | | | | | 1030 | | | | | 1035 | | | | | 1040 |
| Thr | Cys | Ile | Ile | Thr | Phe | Asp | Lys | Asp | Pro | Asn | Ala | Glu | Phe | Val | Thr |
| | | | | 1045 | | | | | 1050 | | | | | 1055 |
| Leu | Met | Arg | Asp | Pro | Gln | Ala | Leu | Gly | Ser | Glu | Arg | Gln | Ala | Lys | Ile |
| | | | 1060 | | | | | 1065 | | | | | 1070 |
| Thr | Ser | Glu | Ile | Asn | Arg | Leu | Ala | Val | Thr | Glu | Val | Leu | Ser | Thr | Ala |
| | | | 1075 | | | | | 1080 | | | | | 1085 |
| Pro | Asn | Lys | Ile | Phe | Ser | Lys | Ser | Ala | Gln | His | Tyr | Thr | Thr | Thr | Glu |
| | | | 1090 | | | | 1095 | | | | | 1100 |
| Ile | Asp | Leu | Asn | Asp | Ile | Met | Gln | Asn | Ile | Glu | Pro | Thr | Tyr | Pro | His |
| 1105 | | | | | 1110 | | | | | 1115 | | | | | 1120 |
| Gly | Leu | Arg | Val | Val | Tyr | Glu | Ser | Leu | Pro | Phe | Tyr | Lys | Ala | Glu | Lys |

```
                        1125                         1130                         1135
    Ile  Val  Asn  Leu  Ile  Ser  Gly  Thr  Lys  Ser  Ile  Thr  Asn  Ile  Leu  Glu
                        1140                         1145                         1150
    Lys  Thr  Ser  Ala  Ile  Asp  Leu  Thr  Asp  Ile  Asp  Arg  Ala  Thr  Glu  Met
                        1155                         1160                         1165
    Met  Arg  Lys  Asn  Ile  Thr  Leu  Leu  Ile  Arg  Ile  Leu  Pro  Leu  Asp  Cys
                        1170                         1175                         1180
    Asn  Arg  Asp  Lys  Arg  Glu  Ile  Leu  Ser  Met  Glu  Asn  Leu  Ser  Ile  Thr
    1185                         1190                         1195                         1200
    Glu  Leu  Ser  Lys  Tyr  Val  Arg  Glu  Arg  Ser  Trp  Ser  Leu  Ser  Asn  Ile
                        1205                         1210                         1215
    Val  Gly  Val  Thr  Ser  Pro  Ser  Ile  Met  Tyr  Thr  Met  Asp  Ile  Lys  Tyr
                        1220                         1225                         1230
    Thr  Thr  Ser  Thr  Ile  Ser  Ser  Gly  Ile  Ile  Ile  Glu  Lys  Tyr  Asn  Val
                        1235                         1240                         1245
    Asn  Ser  Leu  Thr  Arg  Gly  Glu  Arg  Gly  Pro  Thr  Lys  Pro  Trp  Val  Gly
                        1250                         1255                         1260
    Ser  Ser  Thr  Gln  Glu  Lys  Lys  Thr  Met  Pro  Val  Tyr  Asn  Arg  Gln  Val
    1265                         1270                         1275                         1280
    Leu  Thr  Lys  Lys  Gln  Arg  Asp  Gln  Ile  Asp  Leu  Leu  Ala  Lys  Leu  Asp
                        1285                         1290                         1295
    Trp  Val  Tyr  Ala  Ser  Ile  Asp  Asn  Lys  Asp  Glu  Phe  Met  Glu  Glu  Leu
                        1300                         1305                         1310
    Ser  Ile  Gly  Thr  Leu  Gly  Leu  Thr  Tyr  Glu  Lys  Ala  Lys  Lys  Leu  Phe
                        1315                         1320                         1325
    Pro  Gln  Tyr  Leu  Ser  Val  Asn  Tyr  Leu  His  Arg  Leu  Thr  Val  Ser  Ser
                        1330                         1335                         1340
    Arg  Pro  Cys  Glu  Phe  Pro  Ala  Ser  Ile  Pro  Ala  Tyr  Arg  Thr  Thr  Asn
    1345                         1350                         1355                         1360
    Tyr  His  Phe  Asp  Thr  Ser  Pro  Ile  Asn  Arg  Ile  Leu  Thr  Glu  Lys  Tyr
                        1365                         1370                         1375
    Gly  Asp  Glu  Asp  Ile  Asp  Ile  Val  Phe  Gln  Asn  Cys  Ile  Ser  Phe  Gly
                        1380                         1385                         1390
    Leu  Ser  Leu  Met  Ser  Val  Val  Glu  Gln  Phe  Thr  Asn  Val  Cys  Pro  Asn
                        1395                         1400                         1405
    Arg  Ile  Ile  Leu  Ile  Pro  Lys  Leu  Asn  Glu  Ile  His  Leu  Met  Lys  Pro
                        1410                         1415                         1420
    Pro  Ile  Phe  Thr  Gly  Asp  Val  Asp  Ile  His  Lys  Leu  Lys  Gln  Val  Ile
    1425                         1430                         1435                         1440
    Gln  Lys  Gln  His  Met  Phe  Leu  Pro  Asp  Lys  Ile  Ser  Leu  Thr  Gln  Tyr
                        1445                         1450                         1455
    Val  Glu  Leu  Phe  Leu  Ser  Asn  Lys  Thr  Leu  Lys  Ser  Gly  Ser  His  Val
                        1460                         1465                         1470
    Asn  Ser  Asn  Leu  Ile  Leu  Ala  His  Lys  Ile  Ser  Asp  Tyr  Phe  His  Asn
                        1475                         1480                         1485
    Thr  Tyr  Ile  Leu  Ser  Thr  Asn  Leu  Ala  Gly  His  Trp  Ile  Leu  Ile  Ile
                        1490                         1495                         1500
    Gln  Leu  Met  Lys  Asp  Ser  Lys  Gly  Ile  Phe  Glu  Lys  Asp  Trp  Gly  Glu
    1505                         1510                         1515                         1520
    Gly  Tyr  Ile  Thr  Asp  His  Met  Phe  Ile  Asn  Leu  Lys  Val  Phe  Phe  Asn
                        1525                         1530                         1535
    Ala  Tyr  Lys  Thr  Tyr  Leu  Leu  Cys  Phe  His  Lys  Gly  Tyr  Gly  Lys  Ala
                        1540                         1545                         1550
```

-continued

```
Lys Leu Glu Cys Asp Met Asn Thr Ser Asp Leu Leu Cys Val Leu Glu
        1555                1560                1565
Leu Ile Asp Ser Ser Tyr Trp Lys Ser Met Ser Lys Val Phe Leu Glu
        1570                1575                1580
Gln Lys Val Ile Lys Tyr Ile Leu Ser Gln Asp Ala Ser Leu His Arg
1585                1590                1595                1600
Val Lys Gly Cys His Ser Phe Lys Leu Trp Phe Leu Lys Arg Leu Asn
                1605                1610                1615
Val Ala Glu Phe Thr Val Cys Pro Trp Val Val Asn Ile Asp Tyr His
        1620                1625                1630
Pro Thr His Met Lys Ala Ile Leu Thr Tyr Ile Asp Leu Val Arg Met
        1635                1640                1645
Gly Leu Ile Asn Ile Asp Arg Ile His Ile Lys Asn Lys His Lys Phe
        1650                1655                1660
Asn Asp Glu Phe Tyr Thr Ser Asn Leu Phe Tyr Ile Asn Tyr Asn Phe
1665                1670                1675                1680
Ser Asp Asn Thr His Leu Leu Thr Lys His Ile Arg Ile Ala Asn Ser
        1685                1690                1695
Glu Leu Glu Asn Asn Tyr Asn Lys Leu Tyr His Pro Thr Pro Glu Thr
        1700                1705                1710
Leu Glu Asn Ile Leu Ala Asn Pro Ile Lys Ser Asn Asp Lys Lys Thr
        1715                1720                1725
Leu Asn Asp Tyr Cys Ile Gly Lys Asn Val Asp Ser Ile Met Leu Pro
        1730                1735                1740
Leu Leu Ser Asn Lys Lys Leu Ile Lys Ser Ser Ala Met Ile Arg Thr
1745                1750                1755                1760
Asn Tyr Ser Lys Gln Asp Leu Tyr Asn Leu Phe Pro Met Val Val Ile
                1765                1770                1775
Asp Arg Ile Ile Asp His Ser Gly Asn Thr Ala Lys Ser Asn Gln Leu
        1780                1785                1790
Tyr Thr Thr Thr Ser His Gln Ile Ser Leu Val His Asn Ser Thr Ser
        1795                1800                1805
Leu Tyr Cys Met Leu Pro Trp His His Ile Asn Arg Phe Asn Phe Val
        1810                1815                1820
Phe Ser Ser Thr Gly Cys Lys Ile Ser Ile Glu Tyr Ile Leu Lys Asp
1825                1830                1835                1840
Leu Lys Ile Lys Asp Pro Asn Cys Ile Ala Phe Ile Gly Glu Gly Ala
                1845                1850                1855
Gly Asn Leu Leu Leu Arg Thr Val Val Glu Leu His Pro Asp Ile Arg
        1860                1865                1870
Tyr Ile Tyr Arg Ser Leu Lys Asp Cys Asn Asp His Ser Leu Pro Ile
        1875                1880                1885
Glu Phe Leu Arg Leu Tyr Asn Gly His Ile Asn Ile Asp Tyr Gly Glu
        1890                1895                1900
Asn Leu Thr Ile Pro Ala Thr Asp Ala Thr Asn Asn Ile His Trp Ser
1905                1910                1915                1920
Tyr Leu His Ile Lys Phe Ala Glu Pro Ile Ser Leu Phe Val Cys Asp
                1925                1930                1935
Ala Glu Leu Ser Val Thr Val Asn Trp Ser Lys Ile Ile Ile Glu Trp
        1940                1945                1950
Ser Lys His Val Arg Lys Cys Lys Tyr Cys Ser Ser Val Asn Lys Cys
        1955                1960                1965
Met Leu Ile Val Lys Tyr His Ala Gln Asp Asp Ile Asp Phe Lys Leu
        1970                1975                1980
```

-continued

```
Asp Asn Ile Thr Ile Leu Lys Thr Tyr Val Cys Leu Gly Ser Lys Leu
1985            1990                1995                2000

Lys Gly Ser Glu Val Tyr Leu Val Leu Thr Ile Gly Pro Ala Asn Ile
                2005                2010                2015

Phe Pro Val Phe Asn Val Val Gln Asn Ala Lys Leu Ile Leu Ser Arg
                2020                2025            2030

Thr Lys Asn Phe Ile Met Pro Lys Lys Ala Asp Lys Glu Ser Ile Asp
            2035            2040                2045

Ala Asn Ile Lys Ser Leu Ile Pro Phe Leu Cys Tyr Pro Ile Thr Lys
    2050            2055                2060

Lys Gly Ile Asn Thr Ala Leu Ser Lys Leu Lys Ser Val Val Ser Gly
2065            2070                2075                2080

Asp Ile Leu Ser Tyr Ser Ile Ala Gly Arg Asn Glu Val Phe Ser Asn
                2085                2090                2095

Lys Leu Ile Asn His Lys His Met Asn Ile Leu Lys Trp Phe Asn His
            2100            2105            2110

Val Leu Asn Phe Arg Ser Thr Glu Leu Asn Tyr Asn His Leu Tyr Met
        2115            2120            2125

Val Glu Ser Thr Tyr Pro Tyr Leu Ser Glu Leu Leu Asn Ser Leu Thr
    2130            2135            2140

Thr Asn Glu Leu Lys Lys Leu Ile Lys Ile Thr Gly Ser Leu Leu Tyr
2145            2150            2155                2160

Asn Phe His Asn Glu
            2165
```

STRANDED RNA VIRUS PARTICLES

RELATED APPLICATIONS

This application is a continuation-in-part application of U.S. Ser. No. 08/475,587 filed Jun. 7, 1995 now abandoned, which is a continuation-in-part application of U.S. Ser. No. 08/316,438 filed Sep. 30, 1994 U.S. Pat. No. 5,716,821.

GOVERNMENT SUPPORT

The work resulting in this invention was supported in part by certain NIH/NIAID Grants. The U.S. Government may therefore be entitled to certain rights in the invention.

BACKGROUND OF THE INVENTION

Virus families containing enveloped, single-stranded, negative sense (3' to 5') RNA are classified into groups having non-segmented genomes (i.e. order Mononegavirales, which includes the Paramyxoviridae and Rhabdoviridae families) or those having segmented genomes (Orthomyxoviridae, Bunyaviridae and Arenaviridae families).

Of the non-segmented viruses, the Rhabdovirus family is perhaps the most common. Rhabdoviruses cause disease and infect vertebrate and invertebrate animals and plants. For example, the rhabdoviruses that cause rabies and economically important diseases of fish appear to have life cycles confined to vertebrate species. However, all other rhabdoviruses are thought to be transmitted to vertebrates and plants by infected anthropods, which may be the original hosts from which all rhabdoviruses evolved. Characteristically, all rhabdoviruses have a wide host range, although many have been adapted to grow in specific hosts and particularly at the ambient temperature of their hosts.

The viruses of the family Rhabdoviridae known to infect mammals, including humans, have been classified into two genera: the *Vesiculovirus* genus stemming from vesicular stomatitis virus (VSV) and the *Lyssavirus* genus otherwise known as the rabies and rabies-like viruses. The well-characterized viruses of these two genera include: 1) *Genus Vesiculovirus*—VSV—New Jersey, VSV—Indiana, VSV—Alagoas, Cocal, Jurona, Carajas, Maraba, Piry, Calchaqui, Yug Bogdanovac, Isfahan, Chandi pura, Perinet, Porton-S; and 2) *Genus Lyssavirus*—Rabies, Lagos bat, Mokola, Duvenhage, Obodhiang and Ko fon Kan.

VSV has a non-segmented negative-stranded RNA genome of 11, 161 nucleotides that encode five viral proteins: The nucleocapsid protein (N), the phosphoprotein (P, also called NS), the matrix protein (M), the glycoprotein (G) and the RNA-dependent RNA polymerase (L).

The Paramyxovirus family includes the morbilliviruses (e.g., human measles virus, canine distemper virus, rinderpest virus of cattle), the paramyxoviruses (e.g. sendai virus; human para-influenza virus types 1–4; mumps virus; simian virus type 5; and newcastle disease virus) and the pneumoviruses (e.g., human and bovine respiratory syncytial viruses (RSV), pneumovirus of mice and turkey rhinotracheitis virus) genuses.

The pneumovirus human respiratory syncytial virus (hRSV) is the major viral cause of serious lower respiratory tract disease (e.g. bronchiolitis and pneumonia) in infants and children. Similarly, bovine respiratory syncytial virus (bRSV) causes respiratory disease in cattle.

RSV have been isolated from a number of mammals including chimpanzee (Morris, J. A., et al., (1956) *Proc. Soc. Exp. Biol. Med.*, 92, 544–549); humans (Lewis, F. A., et al., (1961) *Med. J. Aust.*, 48, 932–933); cattle (Paccaud, M. F. and C. Jacquier, (1970) *Arch. Gesamte Virusforsch*, 30, 327–342); sheep (Evermann, J. F., et al., (1985) *Am. J. Vet. Res.*, 46, 947–951); and goats (Lehmkuhl, H. D., et al., (1980) *Arch. Virol.*, 65, 269–276). Human RSV (hRSV) have been classified into two subgroups A and B, which include a number of strains (e.g. A2 and 18537). A number of strains of bovine RSV (bRSV) have also been identified (e.g. A51908 and 391-2).

hRSV genomic RNA is approximately 15.2 kb in length. Transcription of the genome initiates at the 3' extracistronic region and proceeds in a sequential polar fashion to yield 10 mRNAs each encoding a major polypeptide. The hRSV genome also has a 44 nucleotide (nt) leader at the 3' end and a 155 nt noncoding trailer sequence at the 5' end (Mink, M. A., et al., (1991) *Virology* 185, 615–624). Proceeding from 3' to 5' on the genome, wild type hRSV includes the following 10 genes: NS 1 and NS2 (also referred to as 1C and 1B), which encode two non-structural proteins; N, which encodes the nucleocapsid protein; P, the phosphoprotein; M, the matrix protein; SH, a small hydrophobic protein; G, the attachment glycoprotein; F, the fusion protein; 22K, a second matrix-like protein and L, which encodes the RNA-dependent, RNA polymerase.

Complete nucleotide sequences have been determined for the nine smaller RSV genes (Collins, Peter L., (1991) *The Molecular Biology of Human Respiratory Syncytial Virus (RSV) of the Genus Pneumovirus* in The Viruses, Frankel Conrat & Kobert Wagner (ed. David Kingsbury Plenum, New York; Collins, P. L. et. al., (1991) *Proc. Natl. Acad. Sci. USA* 88:9663–9667; Sullender, W. M. et. al., (1991) *J. of Virology* 65: 5425–5434; Sullender, W. M. et. al., (1990) *Virology* 178:195–203; Collins, P. L. and G. W. Wertz, (1985) *Virology* 141:283–291; P. L. Collins and G. W. Wertz,(1985) *J. of Virology* 54:65–71; Collins, P. L. and G. W. Wertz (1985) *Virology* 143:442–451; Collins, P. L. et. al., (1985) *Virology* 146: 69–77; Collins, P. L. et. al., (1984) *J. of Virology* 49: 572–578; Satake, M. et. al., (1984) *Journal of Virology* 52: 991–994; Collins, P. L. and G. W. Wertz (1983) *Proc. Natl. Acad. Sci. USA* 80: 3208–3212). In addition, a functional cDNA encoding functional RNA-dependent RNA polymerase was identified as described in the Example. This novel cDNA is disclosed herein as SEQ ID NO: 1. Modifications (e.g. base substitutions) of this exact nucleotide sequence can be performed by one of skill in the art and modified sequences can be tested for functional activity using the system for recovering replicable RS virus RNAs entirely from cDNA clones as described in Example 1.

The bRSV genome encodes 10 proteins that correspond closely in size to the hRSV proteins (Lerch, R. A., (1989) *Journal of Virology*, 63, 833–840). Complete nucleotide sequences have been determined for the N (Amann, V. L., (1992) *Journal of General Virology*, 73 999–1003); F (Lerch, R. A., et al., (1991) *Virology*, 181, 118–131) and G (Lerch, R. A. et al., (1990) *Journal of Virology*, 64, 5559–5569) proteins. cDNA clones corresponding to 9 of the 10 bRSV mRNAs (all but the L protein) have been constructed (Lerch, R. A. et al., (1989) *Journal of Virology*, 63, 833–840).

Although infectious respiratory disease caused by hRSV infection is responsible for an estimated 2.2 million human deaths annually, the majority in infancy (Pringle, C. R. (1991) *Bulletin of the World Health Organization* 65:133–137), and bRSV epidemics in cattle (particularly in winter) are of economic significance to the beef industry (Bohlender, R. E., et al., (1982) *Mod. Vet. Pract.* 63, 613–618; Stott, E. J. and G. Taylor, (1985) *Arch. Virol*, 84, 1–52; Stott, E. J., et al., (1980) *J. Hyg.* Vol. 85, 257–270), no effective vaccine against hRSV or bRSV is yet available.

This unfortunate situation is compounded by the fact that maternal antibodies do not confer solid immunity on neonates (Stott, E. J. et. al., (1987) *Journal of Virology* 60, 607–613) and natural infection affords only partial protection against frequent repeat infections, as immunity to hRSV is complex, involving both antibody and cell-mediated response (Stott, E. J and G. Taylor (1989) Immunity to Respiratory Syncytial Virus p. 85–104. In Immune Responses, Virus Infections and Disease, N. J. Dimmock, and P. D. Minor, (ed.), vol. 27. IRL Press, Oxford).

A disturbing aspect of the immune pathology of hRSV induced respiratory disease was revealed when a formalin inactivated vaccine was tested. Although the vaccine was antigenic and elicited neutralizing antibody, it failed to protect against subsequent infection, and in fact, its use resulted in enhanced frequency and severity of lower respiratory tract disease in children exposed to subsequent reinfection (Fulginiti, V. A. et. al., (1969) *American Journal of Epidemiology* 89, 435–448 and Kim, H et. al., (1969) *American Journal of Epidemiology* 89, 422–434). It is still unclear why the formalin inactivated live virus vaccine failed.

Naturally attenuated RSV vaccines have been prepared (for example by serially passaging virulent respiratory syncytial virus in human diploid lung fibroblasts see U.S. Pat. Nos. 4,122,167 and 4,145,252 to Buynak and Hilleman; and/or by cold-passage or introduction of mutations which produce viruses having a temperature sensitive or cold adapted phenotype see WO 93/21320 to Murphy et. al.). However, attenuated RSV live virus vaccines have proven to be poorly infectious and overall ineffective in the prevention of respiratory syncytial virus mediated disease.

To address this major health problem, work over the past ten years has focused on the molecular biology of hRSV. cDNAs to all of the RS virus mRNAs have been characterized and used to demonstrate that the negative strand RNA genome of the RS virus possesses 10 genes encoding 10 unique polypeptides (Collins, P. L., Huang, Y. T. and G. W. Wertz (1984) *Journal of Virology* 49, 572–578). The possession of 10 genes sets RS virus apart from other paramyxoviruses, which have only six or seven genes. The RS virus genes, proceeding in order from 3' to 5' on the genome are: NS1 and NS2, which encode two non-structural proteins; N, which encodes the nucleocapsid protein; P, the phosphoprotein; M, the matrix protein; SH, a small hydrophobic protein; G, the attachment glycoprotein; F, the fusion protein; 22K, a second matrix-like protein and L, which encodes the RNA-dependent, RNA polymerase.

Based on the identification of RSV genes and encoded proteins, a variety of vaccines have been prepared. For example, U.S. Pat. No. 5,149,650 by Wertz et. al., describes hRSV subunit vaccines comprising recombinant human RSV (rhRSV) structural proteins. U.S. Pat. No. 5,223,254 by Paradiso et. al., describes rhRSV subunit vaccines comprising polypeptides related to a neutralizing epitope, a fusion epitope, or both, of RS virus glycoproteins, including the F and/or G protein of hRSV, as well as viral vaccines encoding the polypeptides. U.S. Pat. No. 5,288,630 by Wathen et. al., describes vaccines made from DNA viruses such as vaccinia expressing an FG rhRSV chimeric protein. However, none of the currently available vaccines have proven to be both safe and effective at immunizing a subject against RSV infection.

Recombinant DNA techniques (including the use of site specific mutagenesis) offer the possibility of designing highly effective vaccines based on RSV whole or partial viral genomes. However, the RNA of negative stranded viruses is not by itself competent to initiate infection or replication (Huang, Y. T., Collins, P. L. and G. W. Wertz (1985) *Virus Research* 2, 157–173). In virions or intracellularly, RSV RNA is always found tightly encapsidated in a ribonucleoprotein core. This nucleocapsid provides the proteins necessary for transcription and replication and is the minimal unit of infectivity.

Although one group has used recombinant techniques to produce synthetic RSV particles from cDNA (Collins, P. L., et. al., (1991) *Proc. Natl. Acad. Sci. USA* 88, 9663–9667), wild type hRSV helper virus was used to provide the proteins required for transcription and replication. Contamination by the wild type helper virus, however, makes this method unsuitable for RSV vaccine preparations. In addition, this system works at low efficiency, so that a reporter gene or strong positive selection is required to detect expression from a virus containing the rescued RNA.

The inventors and co-workers have described a method for recovering an infectious 2.2kb defective interfering particle of vesicular stomatitis virus (VSV) from a cDNA clone by a method that does not require the presence of wildtype helper virus (Pattnaik, A. K. et. al., (1992) *Cell* 69:1011–1020).

A means for generating non-segmented, negative sense virus particles that are not contaminated by wild type helper virus would be useful for producing safe and effective vaccines, gene therapy vectors, and antiviral agents.

SUMMARY OF THE INVENTION

In a first aspect, the invention features negative stranded, non-segmented virus particles, which can be formulated as vaccines, gene therapy vectors or anti-viral agents. At least three different categories of particles can be made, each depending on the inclusion or exclusion of viral genes required for various steps in the replication process (i.e., transcription, genome replication, encapsidation, assembly and release of infectious particles).

One type of non-segmented virus particle, a replicating, spreading virus particle, comprises: i) a non-segmented virus RNA dependent RNA polymerase (L); ii) a non-segmented virus phosphoprotein (P); iii) a non-segmented virus nucleocapsid (N); iv) necessary non-segmented virus structural proteins; v) a 3' non-coding RNA sequence; vi) a 3' to 5' RNA coding region, which encodes the viral proteins required to support viral particle transcription and replication in a newly infected cell and production and assembly of budded infectious particles (i.e. (i)–(iv) above) and optionally includes a heterologous gene (X); and vii) a 5' non-coding RNA sequence. Since these particles can infect cells, replicate their genome, transcribe encoded gene(s), and produce and assemble budded infectious particles, they can effect a long-lasting immunity or gene therapy in a subject.

Another non-segmented virus particle, a replicating, non-spreading virus particle, comprises: i) a non-segmented virus L protein; ii) a non-segmented virus P protein; iii) a non-segmented virus N protein; iv) necessary non-segmented virus structural proteins; v) a 3' non-coding RNA sequence; vi) a 3' to 5' RNA coding region, which encodes the viral proteins required to support viral particle transcription, replication and nucleocapsid assembly in a newly infected cell, but not production and assembly of budded infectious particles (i.e. (i)–(iv) above), and optionally includes a heterologous gene (X); and vi) a 5' non-coding RNA sequence. These particles can infect cells, replicate their genome and transcribe encoded gene(s), which can then be expressed in that cell. However, because they do not encode structural proteins required to produce and assemble budded infectious particles, the particles are incapable of budding off virions and spreading to other cells. These particles are particularly useful as vaccines or gene therapy vectors in applications where it is desirable to control (limit) expression of encoded genes (e.g. antigenic or therapeutic proteins or peptides) by controlling the nuinber of cells infected.

A further non-segmented virus particle, a non-segmented virus transcribing particle, comprises: i) a non-segmented virus L protein; ii) a non-segmented virus P protein; iii) a non-segmented virus N protein; iv) necessary non-segmented virus structural proteins; v) a 3' non-coding RNA sequence, vi) a 3' to 5' RNA coding region which contains an appropriate transcription initiation sequence and a heterologous gene (); and vii) a 5' non-coding RNA sequence. These transcribing particles can transcribe the heterologous gene, but can not replicate in or kill host cells. These particles can therefore be safely used as vaccines and gene therapeutics. In a preferred embodiment, the 3' non-coding sequence is the complement of the 5' non-coding sequence, so that these particles can out-compete wild type virus for proteins required for transcription and replication and therefore can be administered to a subject, for example, as an antiviral agent.

In another aspect, the invention features a novel cDNA encoding a functional respiratory syncytial virus (RSV), RNA dependent, RNA polymerase (L) protein. This cDNA has utility not only in generating recombinant RSV particles, but also in drug screening assays to identify drugs that specifically inhibit or interfere with RSV L protein function and that therefore would function as highly effective antiviral therapeutics for treating respiratory syncytial virus infection.

Recombinant, non-segmented negative stranded virus particles made as described herein are "pure" (i.e., not contaminated by negative strand helper virus). In addition, various types of particles can be formulated in accordance with the intended use. For example, replicating, spreading particles can be formulated and used as vaccines or gene therapy vectors, where widespread and sustained expression of antigenic or therapeutic proteins is desired. Alternatively, replicating, non-spreading particles can be used as vaccines or gene therapy vectors, where limited or controlled expression of antigenic or therapeutic proteins is desired. Transcribing virus particles, on the other hand, can be administered as transient vaccine or gene therapy vectors or as anti-viral agents to interfere and prevent replication of wild-type virus.

Further, particles can be formulated to comprise (and encode) particular non-segmented, negative stranded virus proteins, for example, to optimize target cell specificity or to better accomodate particular heterologous genes. For example, particles comprised of the vesicular stomatitis virus (VSV) glycoprotein (G) proteins can infect an extremely broad range of animal cells, while particles comprised of Respiratory Syncytial Virus (RSV) G proteins specifically infect lung epithelia. Other features and advantages will be readily apparent from the following detailed description and claims.

DETAILED DESCRIPTION OF THE INVENTION

Definitions

As used herein, the following terms and phrases shall have the meanings set forth below:

A "heterologous gene (X)" refers to a nucleic acid molecule that is desired to be transcribed or expressed (i.e. transcribed and translated) from a non-segmented, negative stranded RNA virus particle. As described further below, for vaccine formulations, the heterologous gene preferably encodes a protective epitope of a pathogenic organism. For gene therapy formulations, the heterologous gene preferably encodes a protein that supplements a defective (e.g. mutant) or inappropriately expressed protein in a patient or is an antisense or other biologically active nucleic acid molecule.

A "non-segmented, negative stranded RNA virus" or "non-segmented virus" shall refer to a virus, which contains a negative sense (3'-5') non-segmented RNA genome. Non-segmented viruses are typically classified in the order Mononegavirales, which includes the Paramyxoviridae, Rhabdoviridae and Filoviridae (See Background of the Invention).

"pure" shall mean not contaminated by wild-type virus.

"recombinant" refers to generation by recombinant DNA technology.

A "replicating spreading particle" shall refer to a particle comprised of a non-segmented negative stranded RNA virus genome surrounded by non-segmented negative stranded virus proteins. The particle can enter a cell, transcribe encoded genes to yield messenger RNA (mRNA) to generate proteins, replicate the genomic RNA to produce more genomes and from them to produce more mRNA transcripts and assemble the genomes with proteins to produce viral particles which can then spread to other cells for expanded delivery.

A "replicating non-spreading particle" shall refer to a particle comprised of a non-segmented negative stranded RNA virus genome (which is incomplete) surrounded by non-segmented negative stranded virus proteins. The particle can enter a cell, transcribe encoded genes to yield messenger RNA (mRNA) to generate proteins, replicate the genomic RNA to produce more genomes and from them to produce more mRNA transcripts and assemble the genomes with the proteins to produce viral particles which can not spread to other cells because essential genes for assembly have been omitted from that genome.

A "transcribing particle" shall refer to a particle comprised of cDNA, which includes a heterologous gene and an appropriate transcription initiation sequence and is surrounded by non-segmented negative stranded virus proteins. The particle can infect cells and transcribe an encoded heterologous gene to produce messenger RNAs for expression in that cell, but which cannot replicate to produce more genomes and can not assemble and spread to other cells, because genes for replication and assembly are not included in the cDNA.

Figure 7:
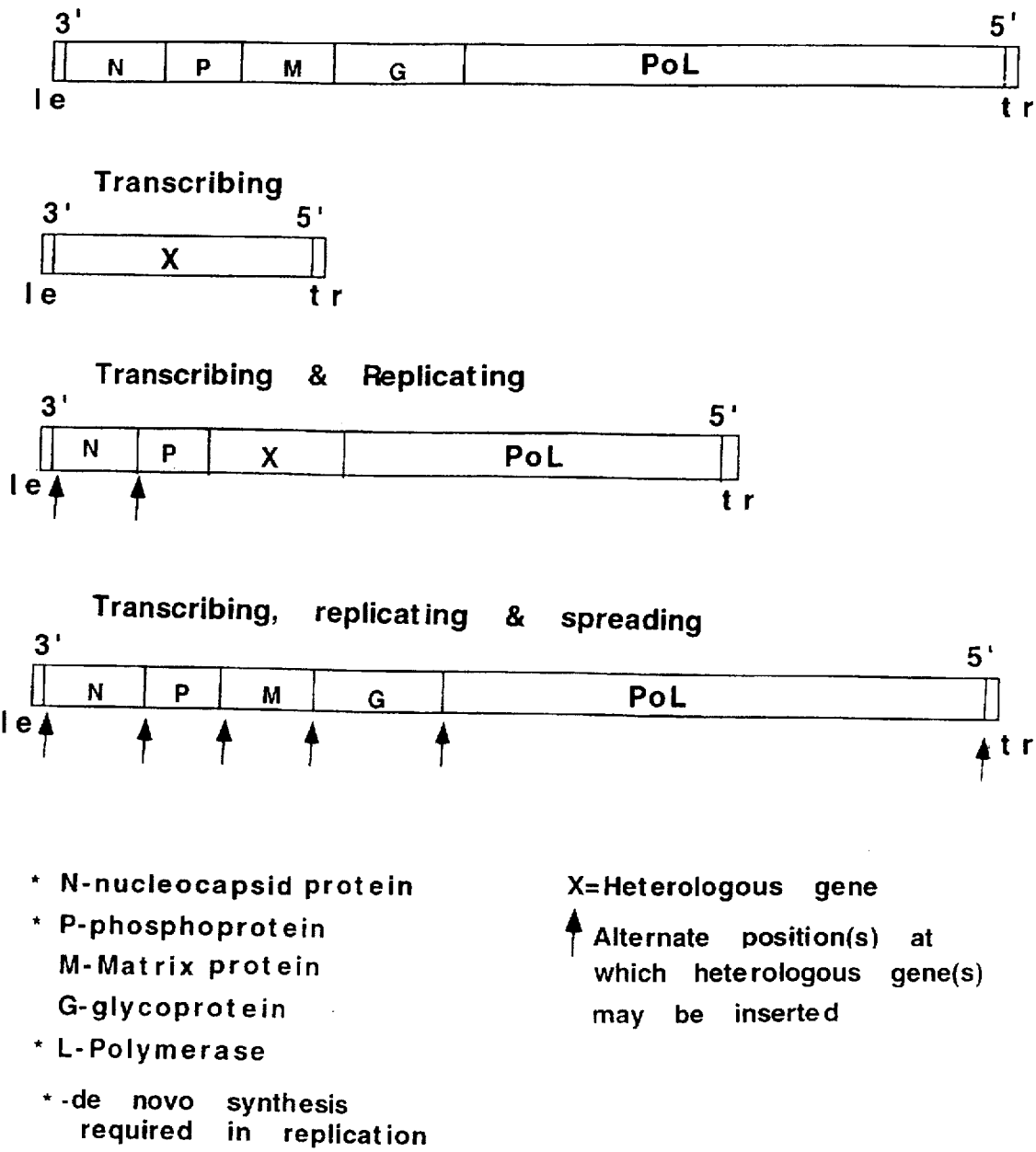
FIG. 7 is a diagrammatic representation of the genome of various VSV particles.

In general, replicating and transcribing non-segmented negative strand RNA virus particles can be generated by introducing into a host cell cDNAs which minimally express the following proteins: i) a non-segmented virus RNA dependent RNA polymerase (L) protein, ii) a non-segmented virus nucleocapsid (N) protein; and iii) a non-segmented virus phosphoprotein (P). Preferably, genes encoding the L, N, and P proteins have been introduced into host cells as plasmids under the control of a promoter region that is recognized by a DNA dependent RNA polymerase, which is native to or has been engineered into the host cell. Into the same host cell is introduced a cDNA plasmid which expresses a non-segmented negative strand genome minimally containing the cis acting signals for RNA replication and transcription (a replicon).

FIG. 1 is a diagrammatic representation of a process for generating RSV ribonucleoprotein (RNP) particles, which are capable of replication, but not of budding virions. Additional non-segmented virus structural proteins can be expressed in host cells in the same manner that non-segmented virus N, P, and L proteins are supplied. Alternatively, additional non-segmented virus structural proteins can be encoded in the cDNA encoding the replicon. A preferred method for making these particles is described in detail in the following Example 1.

In order to make particles that are capable of budding and forming infectious progeny virions, necessary non-segmented virus proteins must also be encoded in the replicon and expressed in a host cell. Preferred RSV structural proteins are selected from the group consisting of RSV N, P, M, M2, SH, G or F proteins. Preferred rhabdovirus (e.g., VSV or rabies virus (RV)) structural proteins include M or G proteins. FIG. 2 is a diagrammatic representation of a process for generating pure, infectious and budding non-segmented viral particles.

As shown in FIGS. 1 and 2, in a preferred method, cDNA encoding the T7 RNA polymerase is introduced into a host cell using the vaccinia virus-T7 RNA polymerase recombinant (Fuerst, T. R. et al., (1986) *Proceedings of the National Academy of Sciences USA* 83, 8122–8126). Plasmids encoding functional proteins (N, P and L) alone (FIG. 1) or in conjunction with structural proteins (FIG. 2) under the control of the T7 promoters are then transfected into the host. Replicons under the control of similar T7 promoters are also transfected into the host cell.

The T7 RNA polymerase transcribes from transfected plasmids the mRNAs to be translated to yield the functional proteins and structural proteins from the replicon cDNA, genomic RNAs with precise termini, which are competent to be replicated and encapsidated to form nucleocapsids. Preferably antigenomic RNAs are expressed in the presence of a pool of nucleocapsid protein and phosphoprotein (i.e. N and P in approximately a 2:1 molar ratio) such that encapsidation of the nascent RNA can begin immediately, thereby enhancing the formation of functional ribonucleoproteins consisting of the RNA and N, P and L proteins.

In a preferred embodiment, the T7 RNA polymerase is expressed from the vaccinia virus strain MVA/T7 Pol recombinant, a highly attenuated and avian host-restricted vaccinia virus recombinant that encodes the T7 polymerase gene (Wyatt, Moss and Rosenblatt, 1995, Virology 210:202–205). Such a vaccinia recombinant is unable to replicate in mammalian cells and hence recovery of viruses from cDNA clones is free not only of helper virus, but also of the recombinant T7 expressing vector.

FIGS. 3 and 4 provide diagrammatic representations of RSV replicons; wildtype (FIG. 3) and panhandle (FIG. 4). For use in the invention, a replicon must include: i) a 3' non-coding RNA sequence, ii) a 3' to 5 RNA coding sequence, and iii) a 5' non-coding sequence. The 3' and 5' non-coding RNA sequences are essential to replication by a non-segmented viral polymerase. As shown in FIGS. 3 and 4, the 5' non-coding sequence can be a trailer sequence (e.g. the RSV 155 nucleotide trailer sequence) and the 3' non-coding sequence can be a leader sequence (e.g. the RSV 44 nucleotide trailer sequence). In general, polymerases of non-segmented viruses are specific to their own leader and trailer sequence.

The replicons shown in FIGS. 3 and 4 employ three basic elements for ensuring intracellular transcription of RNAs with precise termini. A truncated form of the bacteriophage T7 promoter ($\phi 10$) immediately followed by a blunt end cloning site with two blunt-ended restriction sites. The promoter distal site is immediately followed by a cDNA copy of the autolytic ribozyme from the antigenomic strand of hepatitis delta virus (HDV) which, in turn, is immediately followed by a T7 terminator element ($T\phi$). Transcription by the T7 polymerase yields an RNA with two additional nucleotides at the 5' end of the transcript, continuing through the ribozyme and terminating in the $T\phi$ terminator sequence. A precise 3' terminus is generated by the autolytic cleavage of the primary transcript by the HDV genomic RNA at the exact terminus of the RS virus genomic insert.

In between the 3' and 5' non-coding RNA sequences, a replicon contains a 3' to 5' RNA coding region, which includes the viral genes required to support the viral particle transcription, replication and assembly in a newly infected cell plus any heterologous gene (X) desired to be expressed. Each gene encoded in a replicon must have appropriate transcription start and stop signals and intercistronic junctions to signal transcription by the polymerase and subsequent translation to yield protein. Theoretically, there is no limit in the amount of RNA that can be included in the 3' to 5' coding region. In practice, the size of the coding cDNA will be limited by the amount that can be replicated.

An important and essential technical feature for recovering replicating spreading or replicating non-spreading virus particles, in which the 3'-5' coding region comprises a substantial portion of a non-segmented negative stranded RNA virus is the finding that recovery of a complete virus genome into virus particles could only be achieved by expressing a positive (antigenomic) sense copy of the viral RNA, rather than a negative genomic sense RNA as would be expected for a negative sense virus. The requirement for an antigenomic copy may be due to the fact that the RNA polymerase that synthesizes the initial viral RNA in the cell, terminates at each intergenic junction when transcribing a negative sense RNA. However, the polymerase does not terminate at these junctions when transcribing a positive sense RNA. Whether a particular 3'-5' coding region comprising a replicating spreading or replicating non-spreading virus particle must be antigenomic can be determined empirically as described in the following Example 2.

Another technical feature involves the ability to regulate levels of expression of foreign genes inserted into negative strand virus-based vectors by virtue of the location of the genes in the replicon. Control of gene expression in negative strand RNA viruses is a result of a single polymerase entry site at the 3' end of the genome and polymerase dissociation at each intergenic junction. Hence, genes located closest to the 3' end of the genome are transcribed in the greatest amounts and there are decreasing levels of gene expression with increasing distance of a particular gene from the 3' end of the genome. Therefore levels of expression can be increased or decreased by altering the location of the foreign gene insertion relative to the genomic 3' end. Preferred sites of insertion in a VSV genome are shown in FIG. 7.

Eukaryotic cells are preferable "host cells" for producing non-segmented viral particles in vitro. Preferred host cells are mammalian cell lines which are capable of being infected by a non-segmented virus (e.g. HEp-2, HeLa, thymidine kinase deficient (tk-) cells, human embryonic diploid fibroblasts, primary monkey or calf kidney cells, human embryonic kidney, COS, C127, baby hamster kidney (BHK), Vero, LLCMK-2, BSC-1, CV-1, 293 and CHO cells. Non-segmented virus particles comprised of VSV proteins grow to high titers in most animal cells and therefore can be readily prepared in large quantities.

Introduction of replicons into a host cell can be accomplished using standard techniques (e.g. via viral infection, calcium phosphate or calcium chloride co-precipitation, DEAE dextran mediated transfection, lipofection or electroporation). A preferred method of introduction is described in Fuerst, T. R. et. al., (1987) Use of a Vaccinia Virus T7 RNA Polymerase System for Expression of Target Genes. *Mol. Cell. Biol.* 7:2538–44. Cells expressing the infectious viral particles can be cultured in vitro and the particles can be purified using well-known techniques.

As an alternative to production of non-segmented viral particles by in vitro culture, the particles can also be produced in vivo, for example by introducing appropriate expression systems into an animal host having cells that are capable of being infected by the virus and contain (or have been engineered to contain) functional, non-segmented virus L, N and P proteins.

Vaccines

Using the above-described system for replicating pure populations of infectious non-segmented virus particles, a variety of vaccines can be formulated and administered to a subject to induce an immune response against any of a number of pathogenic infections. Preferred vaccine particles include structural proteins obtained from a non-segmented negative stranded virus that is a non-human pathogen and non-oncogenic (e.g. VSV).

The 3' to 5' coding region of appropriate vaccine candidates will include at least one heterologous gene (X) encoding a protective epitope (i.e. an epitope that elicits an immune response in a subject) of a pathogenic bacterium, virus (e.g. HIV, herpes, hepatitis, RSV, parainfluenza virus 3, measles, mumps, rabies, Ebola, Hanta) fungi (e.g. *Candida sp.*) or protozoan (e.g. *Toxoplasma gondii*, ). Table 1 sets forth a representative list of pathogens against which non-segmented viral particle vaccines can be prepared.

TABLE 1

Candidate Pathogens for Vaccine Development

| PATHOGEN | POTENTIAL EFFECTS | CASES PER YEAR (AND DEATHS) | INDUSTRIAL DEMAND |
|---|---|---|---|
| Dengue virus | Fever, shock, internal bleeding | 35,000,000 (15,000+) | Small, (travelers to endemic areas) |
| Intestinal-toxin-producing *Escherichia coli* bacteria | Watery diarrhea, dehydration | 630,000,000 (775,000+) | Small |
| *Hemophilus influenzae* type b bacterium | Meningitis, epiglottal swelling, pneumonia | 800,000 (145,000+) | Great |
| Hepatitis A virus | Malaise, anorexia, vomiting, jaundice | 5,000,000 (14,000) | Small |
| Hepatitis B virus | Same as hepatitis A; Chronic cirrhosis or cancer of liver | 5,000,000 (822,000) | Moderate |
| Japanese encephalitis virus | Encephalitis, meningitis | 42,000 (7,000+) | Small (Travelers) |
| *Mycobacterium leprae* | Leprosy | 1,000,000 (1,000) | None |
| *Neisseria meningitidis* bacterium | Meningitis | 310,000 (35,000+) | Some (during epidemics) |
| Parainfluenza viruses | Bronchitis, pneumonia | 75,000,000 (125,000+) | Great |
| Plasmodium protozoa | Malaria (with anemia, systemic inflammation) | 150,000,000 (1,500,000+) | Moderate (travelers) |
| Rabies virus | Always-fatal meningitis and encephalitis | 35,000 (35,000+) | Small |
| Respiratory syncytial virus | Repeated respiratory infections, pneumonia | 65,000,000 (160,000+) | Great |
| Rotavirus | Diarrhea, dehydration | 140,000,000 (873,000+) | Great |
| *Salmonella typhi* bacterium | Typhoid fever (with platelet and intestinal damage possible) | 30,000,000 (581,000+) | Small (travelers) |
| Shigella bacteria | Diarrhea, dysentery, chronic infections | 250,000,000 (654,000+) | None |
| Streptococcus Group A bacterium | Throat infection, then rheumatic fever, kidney disease | 3,000,000 (52,000+) | Small |
| *Streptococcus pneumoniae* bacterium | Pneumonia, meningitis, serious inflammation of middle ear | 100,000,000 (10,000,000+) | Small to moderate |
| *Vibrio cholerae* bacterium | Cholera (with diarrhea, dehydration) | 7,000,000 (122,000+) | Small (travelers) |
| Yellow fever | Fever, jaundice, kidney damage, bleeding | 85,000 (9,000+) | Small (travelers) |

Alternatively, non-segmented virus particles can be used to infect an appropriate host cell (in vitro or in vivo) for production of recombinant pathogen protective epitopes, which can then be formulated into a "subunit vaccine".

An "effective amount" of live-virus or subunit vaccine prepared as disclosed herein can be administered to a subject (human or animal) alone or in conjunction with an adjuvant (e.g. as described in U.S. Pat. 5,223,254 or Stott et al., (1984) *J. Hyg. Camb.* 251–261) to induce an active immunization against a pathogenic infection. An effective amount is an amount sufficient to confer immunity against the pathogen and can be determined by one of skill in the art using no more than routine experimentation. Determination of an effective amount may take into account such factors as the weight and/or age of the subject and the selected route for administration.

A cocktail of infectious virus particles expressing various pathogen protective epitopes can also be prepared as a vaccine composition. Vaccines can be administered by a variety of methods known in the art. Exemplary modes include oral (e.g. via aerosol), intradermal, intramuscular, intraperitoneal, intravenous, subcutaneous, parental, transdermal and intranasal routes. If necessitated by a particular mode, the vaccine may be encapsulated.

Gene Therapy Vectors

An important application of this technology is the use of non-segmented virus particles for the transcription or expression of heterologous genes (X) from host (e.g., human or animal) cells. Based on the work described in the following examples, it would appear that even very large genes can be accommodated in non-segmented virus particles. VSV based particles are particularly suitable for accomodating large inserts, since VSV has a helical ribonucleocapsid in which there is a linear relationship between genome length and particle size, suggesting that packaging constraints on the amount of additional nucleic acid are minimal.

Furthermore, the levels of expression of foreign genes in non-segmented virus particles can be regulated both by their location within the genome, as explained above, and by altering the adjacent cis-acting sequences that function as promoters. The following Table 2 is a representative list of genes that can be administered to a subject via non-segmented virus particles to treat a disease.

TABLE 2

| Gene therapy | |
|---|---|
| Disease | Therapeutic Gene/Protein |
| IMMUNE DEFICIENCIES | |
| adenosine deaminase deficiency | adenosine deaminase |
| purine nucleoside phosphorylase deficiencies | purine nucleoside phosphorylase |
| osteoporosis | carbonic anhydrase II |
| HEMATOPOIETIC DISORDERS | |
| anemia | erythropoietin |
| thalassemia | α,β thalassemia |
| thrombopenia | thrombopoietin |
| sickle cell disease | anti-sickling globin |
| SERUM PROTEIN DEFICIENCIES | |
| hemophilia (A & B) | factor VIII and factor IX |
| α-1-antitrypsin deficiency | α-1-antitrypsin |
| hereditary angioneurotic edema | C1 esterase inhibitor |
| INBORN METABOLISM ERRORS | |
| urea cycle metabolism | carbamyl phosphate synthetase, ornithine transcarbamylase, argininosuccinate lyase, arginase |
| organic disorders | propionyl CoA carboxylase, methylmalonyl CoA mutase |
| phenylketonuria | phenylalanine hydroxylase |
| galactosemia | galactose-1-phosphate uridyl transferase |
| homocystinuria | cystathionine β-synthase |
| maple syrup urine disease | branched chain 2-keto acid decarboxylase |

TABLE 2-continued

| Gene therapy | |
|---|---|
| Disease | Therapeutic Gene/Protein |
| STORAGE DISEASES | |
| Fabry's disease | galactosidase |
| Gaucher's disease | glucocerebrosidase |
| CNS DISORDERS | |
| Lesch-Nyhan syndrome | hypoxantihine phosphoribosyl transferase |
| Tay-Sachs disease | hexosaminidase |
| FAMILIAL HYPERCHOLESTEROLEMIA | |
| familial hypercholesterolemia | low-density lipoprotein receptor |
| ENDOCRINE DISORDERS | |
| diabetes mellitus | insulin |
| hypopituitarism | growth hormones; growth factors |
| IMMUNOLOGIC DISORDERS | |
| lymphokine deficiencies | interleukins; interferons; cytokines; colony stimulating factors |
| OTHER | |
| Cystic Fibrosis | cystic fibrosis transmembrane conductance regulator protein |
| Duchenne muscular dystrophy | dystrophin |
| cancer, tumors, pathogenic infections | antibodies; antibacterial, antiviral, antifungal and antiprotozoal agents; multidrug resistance and superoxide dismutase |
| wound healing | transforming growth factors |

Alternative to encoding proteins or peptides, non-segmented virus gene therapy vectors can contain antisense oligonucleotides or other nucleic acid biological response modifiers.

A particular non-segmented virus particle can be selected for a particular gene therapy based on the tropism of the natural, wildtype virus. For example, with VSV, target cell specificity is mediated by the attachment of glycoprotein G, which permits the infection of virtually all animal cells that have been studied.

Natural respiratory syncytial virus specifically, on the other hand, only infects respiratory tract tissue (e.g. lung epithelia). Based on this natural affinity, RSV particles can be used as gene therapy vectors for delivery to a subject's respiratory tract. In a preferred embodiment, the protein expressed from an RSV based particle has bioactivity in a subject's lung. In a particularly preferred embodiment, the protein is selected from the group consisting of: the cystic fibrosis transmembrane conductance regulator (CFTR) protein or a functional fragment thereof, an anti protease (e.g. alpha-1-antitrypsin), a tissue inhibitor of metaloproteinase, an antioxidant (e.g., superoxide dismutase), a cytokine (e.g., an interferon), a mucolytic (e.g., DNAse); or a protein which blocks the action of an inflammatory cytokine.

An "effective amount" of a gene therapy vector prepared from a non-segmented viral particle can be administered to a subject (human or animal). An effective amount is an amount sufficient to accomplish the desired therapeutic effect and can be determined by one of skill in the art using no more than routine experimentation. Determination of an effective amount may take into account such factors as the weight and/or age of the subject and the selected route for administration.

Gene therapy vectors can be administered by a variety of methods known in the art. Exemplary modes include oral (e.g. via aerosol), intradermal, intramuscular, intraperitoneal, intravenous, subcutaneous, parenteral, transdermal and intranasal routes. If necessitated by a particular mode, the gene therapy vector may be encapsulated.

In addition to being prepared as a gene therapy pharmaceutical, infectious non-segmented virus particles can be used to infect an appropriate host cell to produce the recombinant protein in vitro (e.g. in a cell culture) or in vivo (e.g. in a transgenic animal).

ANTI-VIRAL AGENTS

Transcribing Particles

Defective interfering particles are subgenomic virus particles (lacking greater or lesser percentages of the virus genome). They contain virus structural proteins and antigens. DI particles require homologous parental (wildtype) virus for replication and replicate preferentially at the expense of helper virus, thereby causing interference. Defective interfering particles can also enhance interferon production, modulate surface expression of viral proteins, affect their transport, processing and turnover, and alter the timing and basic pathology of a virus infection in vivo (Holland, John J., *Defective Interfering Rhabdoviruses*, Dept. of Biology, University of California at San Diego, La Jolla, Calif. 92093, Chapter 8, pp. 297–360).

Figure 4:
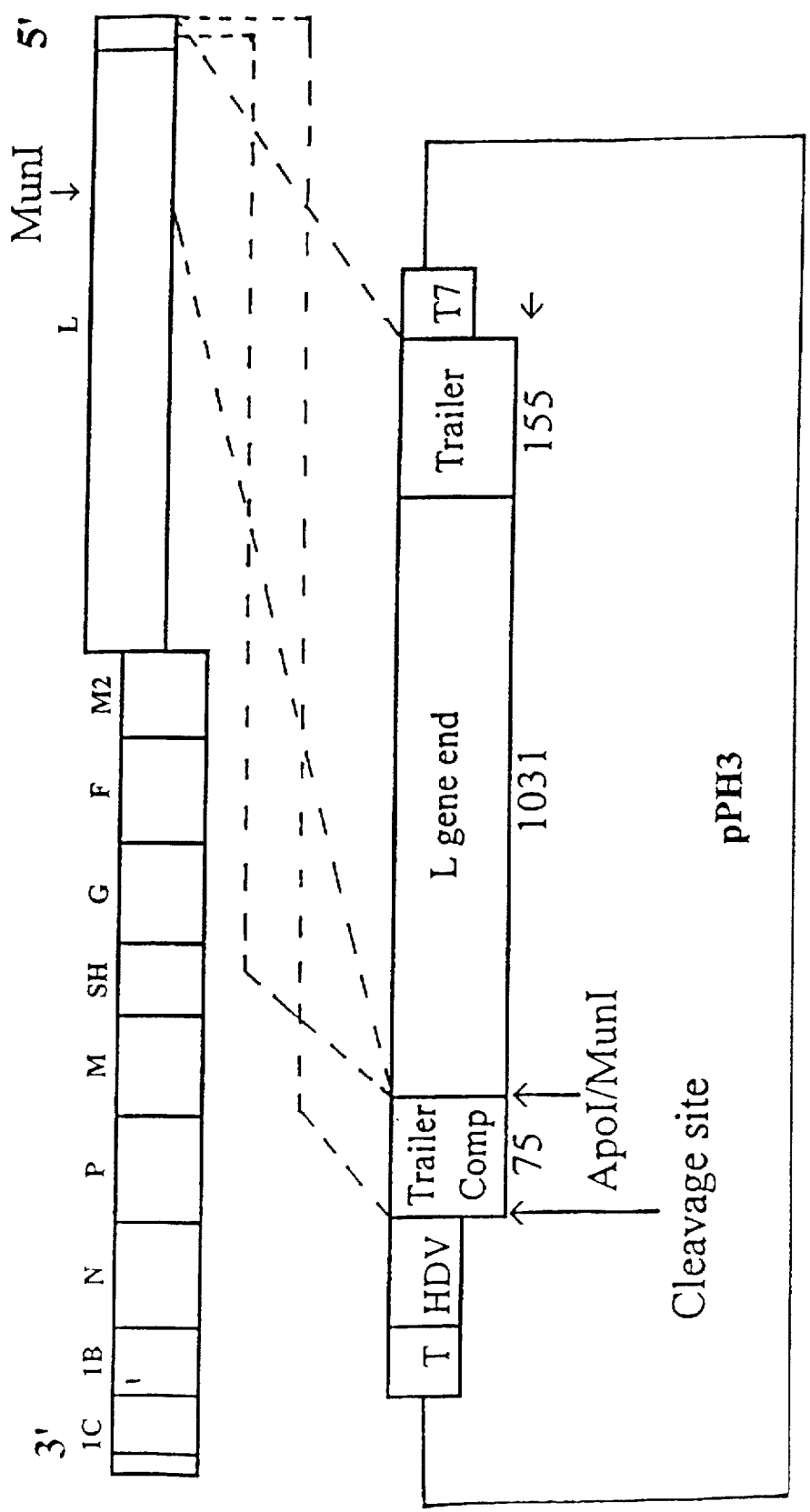
FIG. 4 is a diagrammatic representation of an RSV cDNA panhandle replicon, which can be used in making transcribing particles.
Figure 5:
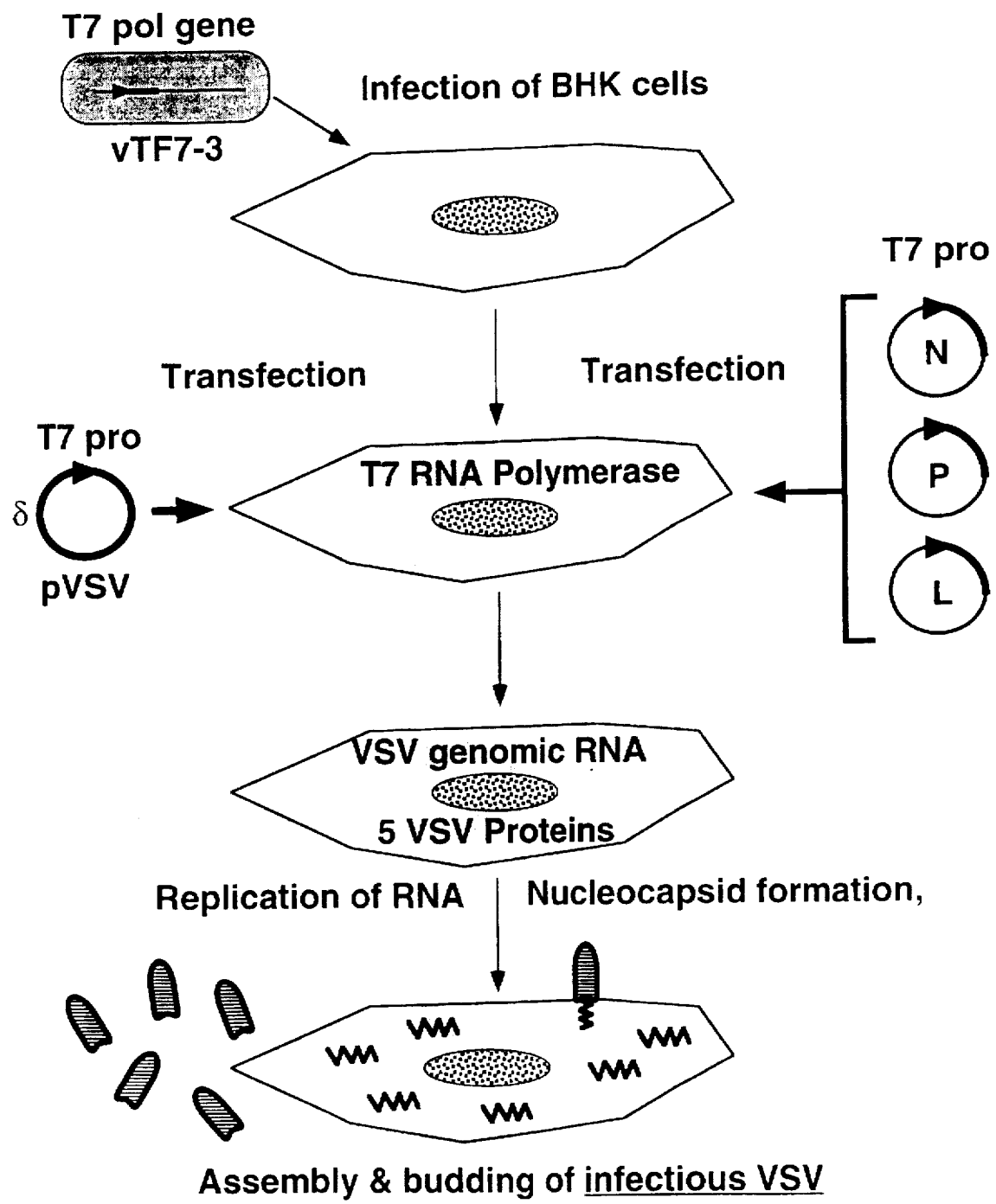
FIG. 5 is a diagrammatic representation of a process for generating recombinant Vesicular Stomatitis Virus (VSV) particles by transfecting the genome into cells expressing only the three genes, N, P and L. The other genes are encoded in the replicon (pVSV).
Figure 6:
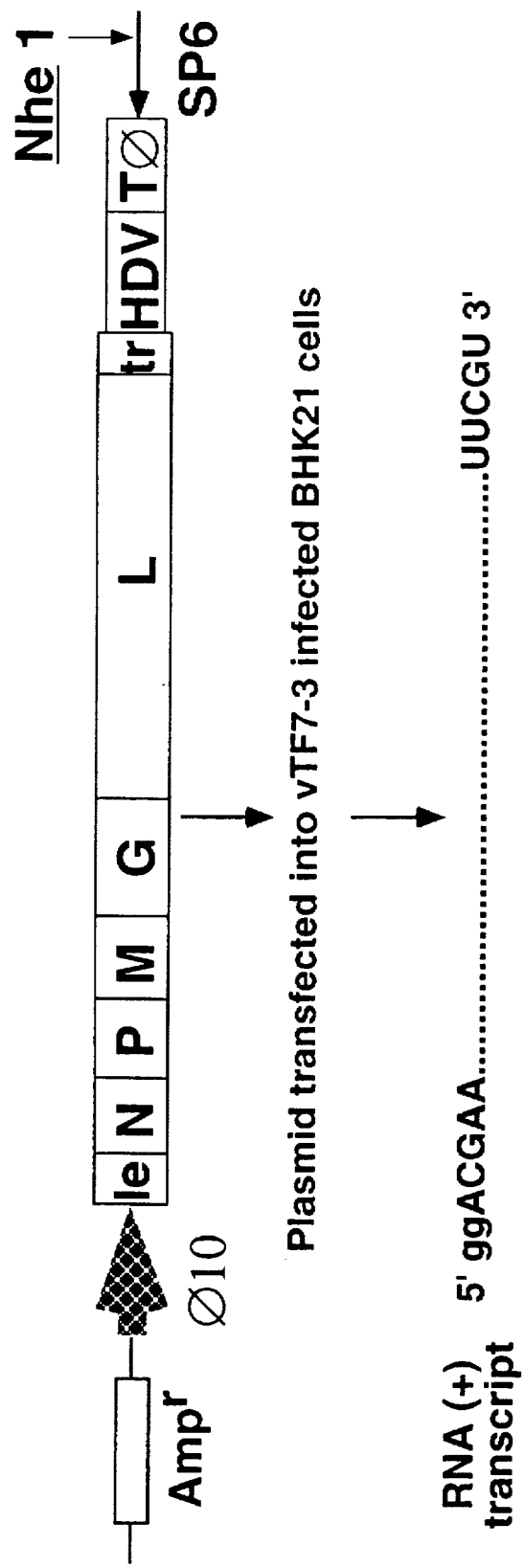
FIG. 6 is a schematic representation of the pVSV1(+) replicon and its T7 transcript.

As described in detail in the following Example, defective interfering-like particles, replicating particles have been made using the panhandle RSV replicon shown in FIG. 4. The panhandle construct contains an authentic 5' terminus and its complement at the 3' terminus as found in copy-back DI RNAs of other negative strand viruses. These replicating particles can out-compete wild type virus for proteins required for transcription and replication and therefore can be administered to a subject as an antiviral agent.

Other replicating and transcribing particles can comprise: i) a non-segmented virus L protein; ii) a non-segmented virus P protein, iii) a non-segmented virus N protein, iv) a 3' non-coding RNA sequence, v) a 3' to 5' RNA coding region, which contains an appropriate transcription initiator and encodes a heterologous gene, and vi) a 5' non-coding RNA sequence can be designed. Preferable replicating and transcribing particles, (i.e. transcribing particles with the greatest replicative advantage) maximize the extent of terminal complementarity between the 3' and 5' non-coding sequences and still maintain a transcription start site. Work with copy-back like VSV particles, has shown that the extent of complementarity, rather than their exact sequence, is a major determinant of whether a template predominantly directs transcription or replication (Wertz, G. et al., (1994) *Proc. Natl. Acad. Sci. USA,*, 91, 8587–8591).

Drug Screening

Effective antiviral drugs specifically prevent or neutralize viral infectivity without affecting host cells. Because the RNA dependent RNA polymerase performs a function unique to negative stranded RNA viruses, a drug that could interfere with the function would be a useful therapeutic against RSV mediated disease. Host cells expressing RSV RNA dependent RNA polymerase as described herein can be used as screens to test various drug candidates for anti-respiratory syncytial virus activity. For example, one can infect cells with VVTF7-3, transfect in the plasmids for N,P,L and suitable RSV mini genomes and measure the effect of drugs on RSV specific RNA replication and transcription, for example, using suitable radiolabelling techniques. This could be accomplished as a screen in cells in culture.

An "effective amount" of an antiviral compound, such as a defective interfering particle or drugs specifically interfering with the replication or transcription of a non-segmented virus, can be administered to a subject (human or animal). An effective amount is an amount sufficient to alleviate or eliminate the symptoms associated with viral infection. The effective amount for a particular antiviral agent can be determined by one of skill in the art using no more than routine experimentation. Determination of an effective amount may take into account such factors as the weight and/or age of the subject and the selected route for administration.

Antiviral agents can be administered by a variety of methods known in the art. Exemplary modes include oral (e.g. via aerosol), intradermal, intramuscular, intraperitoneal, intravenous, subcutaneous, parental, transdermal and intranasal routes. If necessitated by a particular mode, the gene therapy vector may be encapsulated.

The present invention is further illustrated by the following examples, which should not be construed as limiting in any way. The contents of all cited references (including literature references, issued patents, published patent applications, and co-pending patent applications) cited throughout this application are hereby expressly incorporated by reference.

EXAMPLE 1

Functional cDNA Clones of RSV N, P and L Proteins Support Replication of RSV Genomic RNA Analogs and Define Minimal Trans-acting Requirements for Replicating Materials and Methods Construction of Full Length cDNAs Encoding the RS Virus N, P and L Proteins All procedures and reaction conditions for plasmid constructions were carried out according to standard methods (Sambrook et al., (1989) Molecular Cloning: A Laboratory Manual, Cold Spring Harbor Laboratory Press, Cold Spring Harbor, N.Y.). The plasmid constructs were verified by DNA sequence determination of the relevant regions by the dideoxy chain termination method using denatured plasmid DNA as templates (Haltiner, M. et al., (1985) *Nucleic Acids Research* 1015–1028).

In order to express RS virus proteins in the VVT7 based reverse genetic analysis system, cDNA clones of the RS virus N, P and L genes were cloned into pGEM3 vectors downstream of the T7 RNA polymerase promoter, the clones were designated pRSV-N, pRSV-P and pRSV-L, respectively. Briefly, pRSV-N was prepared by transferring a BamHI-PstI fragment containing the entire N gene from pAQ330 (King et al., (1987) *Journal of Virology* 61, 2885–2890) into a pGEM3 vector. cDNA encoding the P protein was generated by reverse transcription of RS virus genomic RNA, followed by PCR amplification with a pair of oligonucleotide primers corresponding to nt positions 2328–2349 and 3459–3443 of the genome (Galinski 1991), respectively. The cDNA was then cloned into the Kpnl-BamHI site of pGEM3. Because of the size of the L gene, (6,578 nt, Stec et al., (1991) *Virology* 183, 273–287), the full-length L gene clones were constructed through several steps of subcloning and finally by assembling four exchangeable segments. Segment 1 (KpnI-MspI fragment, positions 1–1906 in the L gene), segment 2 (MspI-PflMI fragment, positions 1907–3795) and segment 4 (MunI-PstI fragment, positions 5547–6732) were prepared by reverse transcription and PCR amplification, using three pairs of oligonucleotide primers corresponding to nt positions 1–17 and 1923–1903, 1881–1902 and 3802–3788, and 5420–5441 and 6732–6700 of the L gene, respectively.

Segment 3 (PflMI-MunI fragment) came from an existing clone pRSVL-35 which was prepared by oligo-dT primed cDNA synthesis (Collins and Wertz (1983) *Proceedings of the National Academy of Sciences*, USA 80, 3208–3212). The originally assembled clone yielded a 170 KDa polypeptide on translation. Sequencing analysis revealed that an adenosine residue at nt position 4762 of the L gene had been deleted, resulting in a frame-shift generating a premature stop codon 48 nt downstream of the deletion. This sequence error was repaired by site directed mutagenesis.

Generation of cDNA Clones Encoding RS Virus Genomic Analogs cDNA clones that transcribe two types of RS virus genomic analogs were constructed. The first type (wild-type) contained the authentic 3' and 5' termini of the genome, but deleted the majority of the internal genes, and the second type (Panhandle-type) contained complementary termini, derived from the 5' terminus of the genome, surrounding a partial L gene. Diagrams of these two analogs are shown in FIGS. 1 and 2.

The wild -type analog plasmid (pWT) was prepared as follows: cDNA containing the 3' leader, 1C, 1B, N and part of P genes was synthesized by reverse transcription and followed by PCR amplification with a pair of oligonucleotide primers corresponding to nt positions 1–29 and 2378–2360 of the genome. A 2.3 kb PCR product was cloned into the KpnI-SalI site of pGEM3, and the resulting plasmid was digested with SacI and MunI to release a 0.4kb fragment containing the 3' 44-nt leader and nucleotides 1–375 of the 1C gene. Consequently, this SacI-MunI fragment was fused with a MunI-PstI fragment containing nucleotides 5547–6578 (1031-nt) of the L gene and 155-nt trailer, which was derived from pRSV-L, and cloned into pGEM3. The resulting clone was digested with BsiWI and the termini of the released 1.6kb BsiWI fragment repaired by partial filling with dGTP, dTTP, Klenow (BRL), followed by mung bean nuclease digestion. This generated a blunt-ended DNA fragment whose terminal sequences precisely matched the authentic termini of the RS virus genome. This fragment was then inserted into the SmaI site of a transcription plasmid between the T7 promoter and the antigenomic-strand of hepatitis delta virus (HDV) autolytic ribozyme followed by T7 terminator sequences (Ball, L. A. et al., (1992) *Journal of Virology* 66, 2335–2345.). In this sequence context, the wild-type RNA analog synthesized by the T7 RNA polymerase was predicted to contain two non RS virus GTP residues at the 5' end and, after autolytic cleavage, an exact terminus corresponding to the authentic genome 3' end.

The panhandle-type analog (pPH) was derived from the trailer region and the L gene end sequences. A 1.2kb MunI-PstI fragment containing the L gene 5' end and the trailer region was isolated from pRSV-LS4 and fused with an ApoI-PstI fragment comprising 75 nucleotides of the extreme 5' end of the trailer, and subsequently cloned into the PstI site of pGEM3. The resulting clone was treated the same as described in the wild-type analog construction and finally transferred into the SmaI site of the intracellular transcription plasmid. Therefore, the T7 transcripts from the panhandle type analog plasmid were predicted to contain, after autolytic cleavage, complementary 75-nt termini derived from the trailer, surrounding the 1031-nt L gene end.

Virus Infections and DNA Transfections 293 cells were grown in Dulbecco's Modified Eagle Medium (D-MEM, GIBCO Laboratories) containing 10% heat-inactivated fetal bovine serum (FB S) in 60 mm plates. A subconfluent cell monolayer (about $3\times10^6$ cells per plate) was infected with recombinant vaccinia virus vT7-3 (moi of 10 pfu per cell) that expresses T7 RNA polymerase. After 45 minutes virus absorption, the cells were washed once with D-MEM (without FBS) and then transfected with appropriate plasmid DNAs using lipofectin according to manufacturer's (Bethesda Research Laboratories) instructions. For protein expression, the cells were transfected with 5 μg of pRSV-N, pRSV-P or pRSV-L individually or simultaneously, whereas for RNA replication assay, the cells were transfected with 5 μg of pPH3 or pWT1, and combinations of 5 μg of pRSV-N, 2 μg of pRSV-P and 0.25–2.0 μg of pRSV-L. The transfected cells were then incubated in D-MEM (without FBS) 37° C. for 12–16 hours before labeling with radioisotopes.

Immunoprecipitation and Electrophoretic Analysis of Proteins

For radiolabeling of expressed proteins, at 12 hours posttransfection the cells were incubated in methionine-free medium (GIBCO Laboratories) for 45 minutes and then exposed to [$^{35}$S]methionine (20 μCi/ml, Du Pont/NEN) for 3 hours. Cytoplasmic extracts of cells were prepared and viral specific proteins were immunoprecipitated as described previously (Pattnaik, A. K. and G. W. Wertz, (1990) *Journal of Virology* 64, 2948–2957) by using goat polyclonal antiserum raised against RS virus (Chemicon International). For detecting expression of the L protein, rabbit antisera raised against the L protein specific peptides (three peptides corresponding to amino acid positions 1696–1713, 1721–1733 and 2094–2110, respectively, Stec et al., (1991) *Virology* 183, 273–287) were synthesized by the UAB Protein Synthesis Core Facility, conjugated to KLH and antiserum raised in rabbit by Lampire Biological Laboratories, Inc. A combination of the anti-L-peptide sera was used for immunoprecipitation of the L protein. Immunoprecipitated proteins were analyzed by electrophoresis on 10% polyacrylamide gels and detected by fluorography as described previously (Pattnaik, A. K. and G. W. Wertz, (1990) *Journal of Virology* 64, 2948–2957).

Analysis of RNA Replication

To analyze RNA replication, cells were exposed to [$^3$H] uridine (25 uCi/ml, Du Pont/NEN) between 16–24 hours posttransfection, in the presence, where indicated, of actinomycin D (10 μg/ml, water-soluble mannitol complex; Sigma Chemical Co.) after 30 minutes actinomycin D pretreatment. Cells were harvested and cytoplasmic extracts prepared as described previously. Either total RNA or N-protein encapsidated RNA selected by immunoprecipitation with the goat antiserum, was extracted and analyzed by electrophoresis on 1.75% agarose-urea gels and detected by fluorography (Wertz, G. W. and N. Davis (1981) *Nucleic Acids Research* 9, 6487–6503).

RNA Protection Assay of Replication Products

An RNA protection assay (RPA) was used to detect strand-specific RNA synthesis using an RPA II kit according to manufacturer's instructions (Ambion). Briefly, N-protein encapsided RNAs from one 60 mm plate of cells transfected with pPH3 and the N, P or N, P and L protein plasmids as described above (without radiolabeling and actinomycin D treatment) were selectively enriched by immunoprecipitation and were used in RPA for each reaction. A strand-specific RNA probe was generated by T7 RNA polymerase in vitro transcription of a pGEM3 plasmid with incorporation of [$^{35}$S] UTP (Du Pont/NEN) according to the manufacturer's instructions (New England Biolabs). The pGEM3 plasmid containing a BclI-BglII fragment of the L gene end (positions 5655–6514) was linearized by digestion with SspI, the cleavage site for which is present in the BclI-BglII fragment (position 6158), so that run off T7 polymerase transcription produced a 391-nt RNA probe. The RNA probe was purified by polyacrylamide gel electrophoresis. The specific activity of the purified probe was determined and $6 \times 10^3$ cpm of probe was used in each reaction of the assay. The protected RNA was analyzed by electrophoresis on 4.5% sequencing gels and detected by fluorography.

RESULTS
Expression of RS Virus Proteins

In order to establish a reverse genetic approach for analysis of RS virus, it was necessary to prepare cDNA clones capable of expressing the RS virus proteins involved in RNA replication. By analogy with other negative-stranded RNA viruses, these would most likely be the N, P and L proteins, although at the outset it was unknown whether the nonstructural proteins 1C and 1B might also be required. Full-length cDNA clones of the N, P and L genes were prepared as described and subcloned into the expression vector pGEM3. To detect whether these cDNA clones expressed N, P and L proteins, the recombinant vaccinia virus-T7 RNA polymerase expression system was used. (Fuerst, T. R. et al., (1986) *Proceedings of the National Academy of Sciences USA* 83, 8122–8126). 293 cells were infected with vTF7-3 and transfected with plasmids pRSV-N, pRSV-P, or pRSV-L. At 12 hours posttransfection, the cells were labeled with [$^{35}$S]methionine for 3 hours. Cytoplasmic extracts were prepared, and proteins were immunoprecipitated with anti-RS virus antibody in the case of the N and P proteins, or anti-L-peptide antisera in the case of the L protein, and analyzed by electrophoresis.

vTF7-3 infected cells transfected with pRSV-N expressed a protein which comigrated with the authentic N protein synthesized in RS virus infected cells. Similarly, vTF7-3 infected cells transfected with pRSV-P also expressed a protein which comigrated with the authentic P protein. Neither untransfected nor uninfected cells produced these proteins, suggesting that pRSV-N and pRSV-P expressed the appropriate viral proteins.

A cDNA clone containing the L gene constructed as described above was transfected into vTF7-3 infected cells. The total expressed products were analyzed by SDS-PAGE and a polypeptide with a molecular weight of 170 kDa was observed, but not the expected 250 kDa polypeptide. Sequencing analysis revealed that an adenosine residue at nt position 4762 of the L gene had been deleted, resulting in a frame-shift which generated a premature stop codon 48 nt downstream of the deletion. The sequence error was repaired by restoring the A residue by site-directed mutagenesis. A corrected L gene cDNA clone was constructed and expressed in the same system. In order to detect the L protein, rabbit anti-L-peptide sera were prepared and used to immunoprecipitate the products of expression. The results showed that a polypeptide of 250 Kd expressed from the repaired L gene clone was identified by the anti-L-peptide sera, which comigrated with the authentic L protein. A few faint bands migrating faster than the L protein were also observed, which might be the products derived from late initiations of translation, or degradation of the L protein. This work demonstrated that the corrected full-length L gene clone was capable of directing synthesis of authentic size RS virus L protein. Consequently, this cDNA clone was used in RNA replication experiments to test whether the expressed L protein was a functional polymerase.

Expression of Genomic RNA Analogs

Figure 1:
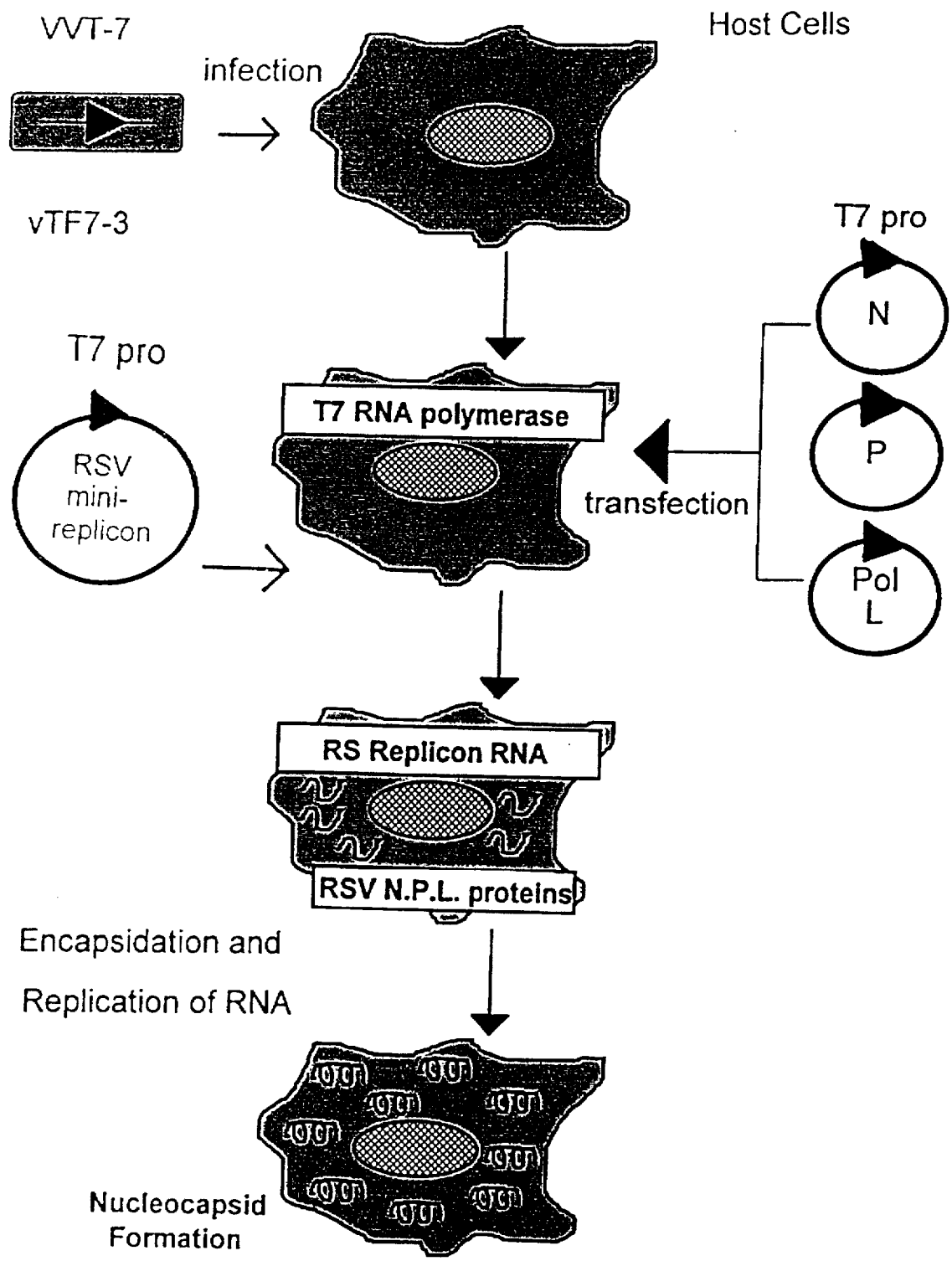
FIG. 1 is a diagrammatic representation of a process for generating replicating, non-spreading Respiratory Syncytial virus (RSV) particles.

To establish the reverse genetic analysis system, cDNA clones that transcribed two types of RS virus genomic RNA analogs were constructed. As shown in FIG. 1, the wild-type cDNA clone, pWT1, encoded an analog of RS virus genomic RNA in which the majority of the internal genes were deleted. Transcription of pWT1 by T7 RNA polymerase would yield a 1605-nt long, negative-sense RNA with the authentic 3' terminus of the RS virus genome, created by the autolytic cleavage of the ribozyme, and the following structural features (listed in 3' to 5' order): (i) the 44-nt leader region; (ii) nt 1-375 of the 1C gene; (iii) nt 5547–6578 (1031-nt) of the L gene; (iv) the 155-nt trailer region and (v) two non RS virus GTP residues encoded by the vector. Similar to pWT1, the panhandle-type cDNA clone, pPH3, encoded an RS virus genomic analog in which most of the internal genes had been deleted.

Figure 2:
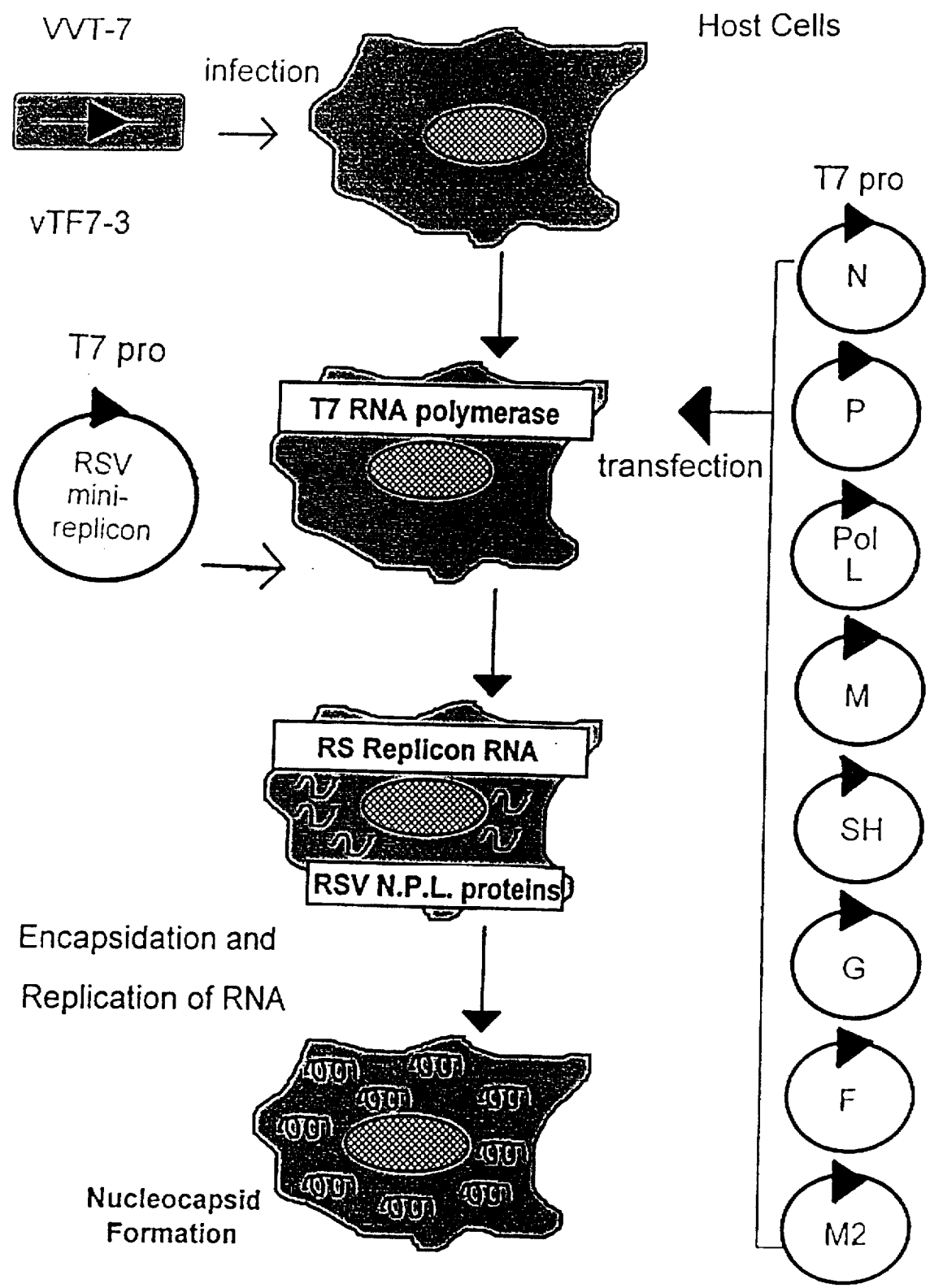
FIG. 2 is a diagrammatic representation of a process for generating replicating and spreading RSV particles.
Figure 3:
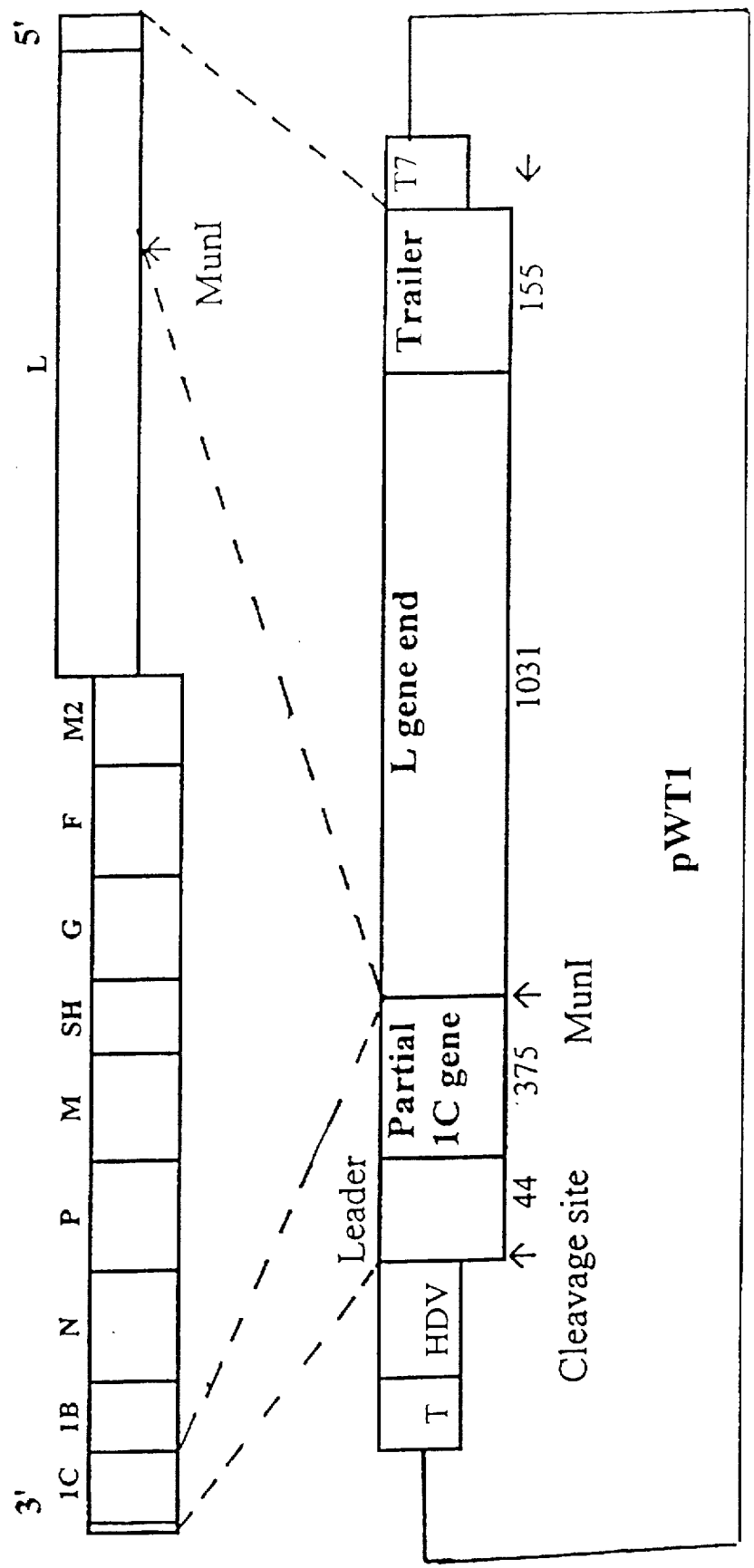
FIG. 3 is a diagrammatic representation of an RSV cDNA wildtype replicon.

However, in contrast to pWT1, pPH3 contained DI-like termini, i.e., complimentary termini surrounding a partial L gene (FIG. 2). As with pWT1, the panhandle-type genomic analog sequences were also placed in the transcription plasmid under T7 promoter control and followed by the HDV ribozyme and T7 terminator. T7 RNA polymerase transcription of pPH3 would produce 1261 -nt long negative-sense RNA consisting of the 155-nt trailer at the 5' end, 75-nt of the trailer's complement at the 3' end and 1031 -nt L gene end in the middle. After autolytic cleavage, the 3' end of the panhandle-type RNA analog should be exactly complementary to the authentic 5' end of the genome.

To examine the ability of these two constructs to generate transcripts of the appropriate length in 293 cells, pWT1 and pPH3 were transfected in to vTF7-3 infected cells, respectively, and RNAs were labeled with [$^3$H]uridine for 8 hours at 16 hours posttransfection. The total cytoplasmic RNA species synthesized during this period was analyzed by electrophoresis on agarose-urea gel. A major species of labeled RNA of 1.6 Kb from the pWT1 transfected sample and 1.2 Kb from the pPH3 transfected sample was observed, but not in vTF7-3 infected only and the uninfected cells. The minor bands migrating slightly slower than the major negative-sense RNA transcripts were RNA that had not undergone the autolytic cleavage by the time of analysis. The identity of these cleaved and uncleaved transcripts was confirmed later by comparison with the cleaved and uncleaved transcripts from the same plasmids generated by in vitro transcription. More than 90% of the transcripts synthesized during the labeling period was cleaved by the ribozyme, releasing a 200 base RNA that contained the ribozyme and terminator sequences and that migrated near the bottom of the gel.

Encapsidation and Replication of Genomic RNA Analogs

The active template for RNA synthesis by negative-strand RNA viruses is the RNA in the form of a ribonucleocapsid. To determine whether the RNAs transcribed in cells by T7 polymerase could be encapsidated with the nucleocapsid protein and replicated, vTF7-3-infected cells were transfected with pWT1 or pPH3 and combinations of plasmids encoding the N, P and L proteins. At 16 hours posttransfection, the cells were exposed to [$^3$H]uridine for 6 hours. Encapsidated and replicated RNAs were selected by immunoprecipitation and analyzed on an agarose-urea gel. Immunoprecipitation of [3H] labeled RNA by anti RS virus polyclonal serum demonstrated that encapsidation of WT and PH type RNA analogs occurred when pRSV-N, pRSV-P and pRSV-L were cotransfected. However, in the absence of pRSV-L, encapsidated RNA was barely detected. These results suggested that only a small percentage of the original T7 negative-sense RNA transcripts was encapsidated and that the majority of the encapsidated RNA arose from replication of the original transcripts by the RS virus polymerase. To test whether the labeled and encapsidated RNA was replicated by the RS virus RNA dependent RNA polymerase, the effect of actinomycin D on synthesis and encapsidation of RNA was analyzed. Actinomycin D inhibits DNA dependent RNA synthesis, but not RNA dependent RNA synthesis.

In the presence of actinomycin D, incorporation of [$^3$H] uridine into RS virus genomic analog was completely blocked when only pRSV-N and pRSV-P were present in the cotransfection. However, when pRSV-L was included in the cotransfection, synthesis of the genomic analog was resistant to the drug and readily detected. The results demonstrated that the RNAs were indeed the products of replication by the RS virus polymerase. The majority of encapsidated RNAs represent the replicated RNAs However, the amount of RNA replicated from the wild-type genomic analog is much less than that from the panhandle one, although a similar molar ratio of plasmids was used in the transfection. Due to its higher RNA replication efficiency, the panhandle type analog pPH3 was used as a model to determine the trans-acting protein requirements for RNA replication and to detect the strand-specific RNA synthesis.

The N, P and L Proteins are the Minimal Trans-Acting Protein requirements for RNA Replication To determine the minimal trans-acting protein requirements for RS virus genomic RNA replication, and to optimize the conditions of RNA replication, pPH3 transfected-cells were cotransfected with various combinations of plasmids encoding the N, P and L proteins. At 16 hours posttransfection, the cells were labeled with [$^3$H]uridine in the presence of actinomycin D for 6 hours. The RNAs extracted from cell lysates were analyzed by electrophoresis on an agarose-urea gel. The results clearly showed that any combination of two of these three plasmids in the cotransfection did not support RNA replication. Only when all three plasmids were present in the cotransfection did replication of the panhandle-type RNA analog occur. This clearly defined that the N, P and L proteins were the minimal trans-acting protein requirements for RNA replication of the RS virus genomic analog. As the amount of pRSV-L was increased from 0.25 μg–1 μg in the cotransfection, the yield of replicated RNA products also increased. However, when 2 μg of pRSV-L was cotransfected, the efficiency of replication no longer increased. Maximum RNA replication occurred when the molar ratio of transfected N, P and L genes was 12:5:1.

To test the specificity of the requirement for the viral RNA dependent RNA polymerase for RS virus RNA replication, a VSV L gene plasmid that had been shown to support VSV RNA replication in a similar system (Pattnaik, A. K. et. al., (1992) Infectious defective interfering particles of VSV from transcripts of a cDNA clone. *Cell* 69:1011–1020; Wertz, G. et al., (1994) *Proc. Natl. Acad. Sci. USA*,, 91, 8587–8591) and atruncated form of RS virus L gene plasmid that expressed a 170 kDa polypeptide were used to replace pRSV-L in the cotransfection. Neither the heterologous VSV RNA polymerase nor the truncated RS virus polymerase supported RNA replication. These data demonstrate that the RNA replication of the genomic analog indeed requires RS virus specific and functional polymerase.

RNase Protection Assay Demonstrates the Synthesis of Positive-Strand RNA

During RNA replication of negative-stranded RNA viruses, the encapsidated negative sense genome must first replicate a positive sense RNA antigenome, which in turn would be encapsidated and serve as a template for the synthesis of progeny negative-sense RNA. Therefore, the synthesis of a positive-strand intermediate is critical evidence for establishing that replication of the original negative-strand RNA has occurred. To test RS virus positive-strand RNA synthesis, an RNase protection assay was carried out with a strand-specific probe. Encapsidated RNA was selected by immunoprecipitation from cells cotransfected with pPH3 and combinations of the N, P and L gene plasmids. A 391-nt long, [$^{35}$S]-labeled RNA probe was used, of which 360 nucleotides were transcribed from the L gene sequences and complementary to the positive-sense RNA, and the other 31 nucleotides corresponded to the polylinker region of the vector. Hybridization of the probe with the positive-strand RNA should produce a double strand RNA hybrid which, after nuclease digestion to remove the overhanging nucleotides, would be 360 base pairs long.

Indeed, electrophoretic analysis of the protected RNA products demonstrated that the positive-strand RNA was synthesized when all three viral N, P and L gene plasmids were cotransfected, but not in the absence of the L gene plasmid in the cotransfection. This protected RNA product migrated at the predicted size (360 nt). The undigested probe (391 nt) hybridized with yeast RNA and was completely degraded following treatment with RNase, thus indicating that the nuclease digestion was complete. These data demonstrated that positive-strand RNA was replicated from the initial negative sense RNA transcribed in cells, and confirmed that RNA replication occurred only when all three viral proteins, N, P and L were provided by cotransfection. The presence of positive-sense RNA was also confirmed by primer extension analysis with a negative-sense oligonucleotide primer.

EXAMPLE 2

Recovery of Infectious VSV Entirely from cDNA Clones

Materials and Methods

Plasmid construction and transfections

A full length cDNA clone of VSV was assembled from clones of each of the VSV genes and intergenic junctions, using standard cloning techniques (Sambrook, J. et al. (1989) *Molecular Cloning: A Laboratory Manual,* 2d ed. Cold Spring Harbor Laboratory Press, New York). Whenever possible, clones that were known to encode functional VSV proteins were used for the construction. These clones were assembled into a full length cDNA and inserted in both orientations between the bacteriophage T7 promoter and a cDNA copy of the self cleaving riobzyme from the antigenomic strand of HDV. The resulting plasmids were named pVSV1(+) and pVSV1(−) to reflect the polarity of the T7 transcript they generated: VSV anti-genomic or genomic RNA respectively. The T7 transcripts contained two non-VSV nucleotides (GG) at their 5' end but were cleaved by the HDV riobzyme to generate a 3' terminus which corresponded precisely to the 3' end of the VSV antigenomic (FIG. 5) or genomic sequence.

Transfection of plasmids into BHK1 cells infected with vTF7-3 was performed using the conditions and quantities of support plasmids described previously (Pattnaik, A. K. et al. (1992) *Cell* 69, 1011–1020), and up to 5 μg of the plasmids pVSV1(+) or pVSV1(−). Transfected cells were incubated at either 31° C. or 37° C. For some experiments, the pVSV1(+) and pVSV1(−) plasmids were linearized by digestion at a unique NheI site located downstream of the T7 terminator in the pGEM3 based plasmids. RNAs made by run-off transcription from these linearized DNAs still contained the HDV ribozyme whose production of a perfect 3' end by self-cleavage is essential for VSV RNA replication (Pattnaik, A.K. et al. (1992) *Cell* 69, 1011–1020). All experiments involving pVSV1(+) were performed in a newly constructed building, in a laboratory in which wild-type VSV had never been used.

To identify cDNA-derived virus unambiguously, several genetic markers were incorporated into the full length cDNA clones. All 5 genes were of the Indiana serotype of VSV, but whereas the N, P, M and L genes originated from the San Juan strain, the G gene (kindly provided by Elliot Lefkowitz) was from the a Orsay strain. In addition the functional P clone has 28 nucleotide sequences differences from the published San Juan sequence and in the case of pVSV 1(+) the 516 nucleotides at the 5' end of the VSV genome originated from pDI, the clone of DI-T RNA (Pattnaik, A. K. et al. (1992) *Cell* 69, 1011–1020). This region contained several nucleotide differences from the published VSV Indiana San Juan sequence. Specifically the nucleotide differences G11038A, A11070C, and an insertion of an A residue at nucleotide 11140 were used to unambiguously distinguish cDNA-derived virus.

To examine the behavior of T7 RNA polymerase at a VSV intergenic junction, a BglII fragment that encompassed the NP intergenic junction of VSV (nucleotides 1236–1685) was inserted in both orientations into the unique BglII site of plasmid 8 (Wertz, G. W. et al (1994) *Proc. Natl. Acad. Sci. USA* 91, 8587–8591). This plasmid contained 210 nucleotides form the 3' end of VSV RNA and 265 nucleotides from the 5' end, joined at a unique BglII site and placed between the T7 promoter and the HDV ribozyme. A positive-sense version of plasmid 8 was generated and used to accommodate the NP intergenic junction sequence in an identical manner. These plasmids were named 8(−) and 8(+) to reflect the polarity of the T7 transcript they generated, with an additional suffix to indicate whether the NP intergenic junction was in the natural (NP) or inverted (PN) orientation with respect to the surrounding VSV sequences (see FIG. 5).

Virus Production and Neutralization

The medium from transfected cells was harvested at 15 to 48 hours post transfection, clarified by centrifugation (14 000×g for 5 minutes), and virus titers were monitored by plaque assay on BSC40 cells in the presence of 25μg per ml cytosine arabinoside (ara-c), to inhibit replication of VV. Neutralization assays of virus were performed by incubation with a mouse polyclonal serum raised against purified VSV, by incubation with antiserum for 30 minutes at room temperature in DMEM. This approach also allowed titration of VV, by plaque assay in the absence of ara-c.

Virus Characterization

Virus amplification, radioactive labeling of RNA with $[^3H]$uridine (33μCi per ml; 1 Ci=37 GBq) and proteins with $[^{35}S]$ methionine (10μCi per ml) or $[^3H]$leucine (50μCi per ml) and their electrophoretic analyses were performed as described previously (Pattnaik, A. K. et al. (1990) *J. Virol.* 64, 2948–2957). Viral RNA was purified from $10^8$ pfu of amplified cDNA-derived VSV and reverse transcribed using AMV reverse transcriptase (Life Sciences) and a primer that annealed to negative-sense RNA at nucleotides 11026–11043 of the VSV genome. Approximately 1/10th of this reaction was used for DNA amplification by PCR. PCR reactions were carried out using the primer described above and a second primer that annealed to the extreme 3' end of positive-sense VSV RNA (nucleotides 11161–11144). PCR products were cloned and sequenced using standard techniques (Sambrook, J. et al. (1989) *Molecular Cloning: A Laboratory Manual*, 2nd ed., Cold Spring Harbor Laboratory Press, New York).

In Vitro Transcription

RNA was generated in vitro using T7 RNA polymerase (GIBCO-BRL) according to manufacturer's instructions, except that rNTP concentrations were elevated to 2.5 mM, and supplemented with $[^3H]$ UTP (80μCi per ml). The RNA products of in vitro transcription were resolved by electrophoresis on 1 % agarose-urea gels and visualized by fluorography. It should be noted that RNA mobility in the pH 3.0 agarose-urea gels is a function of base composition as well as size (Lerach, H., (1977) *Biochemistry*, 16, 4743–4751).

RESULTS

Construction of a Full Length cDNA Clone of VSV and Recovery of Infectious Virus A full-length cDNA of the RNA genome of VSV was assembled from clones of each of the five VSV genes and their intergenic regions and inserted into a pGEM3 based transcription plasmid between the T7 promoter and the HDV ribozyme (FIG. 6). Plasmids containing the cDNA in both orientations were constructed and designated PVSV1(+) and pVSV1(−) to reflect the polarity ofthe T7 transcript they generated: VSV anti-genomic or genomic RNA respectively. pVSV1(+) was transfected into BHK21 cells that expressed T7 RNA polymerase from a VV recombinant, together with T7 transcription plasmids that separately encoded the VSV N, P, and L proteins. These latter three "support" plasmids provided sources of the VSV proteins necessary to support encapsidation of the primary naked transcript, and to provide a source of polymerase for replication and transcription of this RNA. Control transfections included cells that received pVSV1(+) but no support plasmids, and cells that received the support plasmids but no pVSV1(+). After incubation at 31°or 37° C., the culture media were harvested, diluted and monitored by plaque assay for the presence of infectious VSV. Infectious virus was recovered reproducibly from cells that received both pVSV1(+) and the N, P, and L support plasmids, but not in either of the two control transfections in which either pVSV1(+) or the VSV support plasmids were omitted (Table 2). The efficiency of recovery varied among different experiments, and was affected by the time of harvest, the temperature of incubation of the cells, and whether the genomic cDNA plasmid was linearized before transfection. Among the conditions tested, the highest level of recovery was $8\times10^4$ pfu per ml in the 1.5 ml of medium from $10^6$ cells that had received 5μg of linearized pVSV1(+) and been incubated at 31° C. for 45 hours.

TABLE 3

Recovery of Infectious Virus from pVSV1(+)

| VSV Plasmids Transfected | | Virus Yield | Virus Recovered in |
|---|---|---|---|
| Genomic | Support | (pfu/ml) | X/Y transfections |
| pVSV1(+) | — | <10 | 0/8 |
| — | N, P, L | <10 | 0/4 |
| pVSV1(+) | N, P, L | <10 to 8 × $10^4$ | 9/12(a) |
| pVSV1(+) | N, P, L, M, G | <10 to 1 × $10^2$ | 1/6 |
| pVSV1(−) | N, P, L | <10 | 0/27 |
| pVSV1(−) | N, P, L, M, G | <10 | 0/12 |

The only source of the VSV G and M proteins in this experiment was via VSV-mediated transcription of the replicated genomic RNA. Indeed, when support plasmids that expressed the M and G proteins were included in the transfection mixture together with those that expressed N, P and L, under conditions that support the production of infectious VSV DI particles from a DI cDNA clone (Pattnaik, A. K. et al. (1992) *Cell* 69, 1011–1020), the recovery of infectious virus was strongly suppressed (Table 3), perhaps because VSV M protein can inhibit both viral and cellular transcription (Clinton, G. M. et al. (1978) *Cell* 15, 1455–1462; Black, B. L. et al. (1992) *J. Virol.* 66, 4058–4064).

Plasmid pVSV(−) which was designed to express a full-length negative-sense copy of the VSV genome, failed repeatedly to yield infectious virus, either when supported by the expression of N, P, and L proteins, or by the full complement of five VSV proteins (Table 3).

Neutralization of Recovered Virus by Anti-VSV Antiserum

The virus that yielded the plaques was identified as VSV because plaque-formation was completely inhibited by a mouse polyclonal anti-serum raised against purified wild-type VSV. However, since the transfected cells had been infected with the VV recombinant vTF7-3 to provide T7 RNA polymerase, the harvested culture medium also contained infectious VV. Plaque assays performed in the presence of anti-VSV anti-serum (and in the absence of ara-c) showed that under all conditions of transfection, VV titers of $1-2\times10^6$ pfu per ml were released from the infected transfected cells. However, the VV plaques were less than one tenth the size of the VSV plaques, easily distinguished from them, and completely suppressed by ara-c which inhibits VV DNA replication.

RNA and Protein Synthesis Activities of Recovered VSV

To provide further evidence that the virus recovered from transfections of pVSV1(+) was VSV, the RNAs and proteins synthesized by this virus were compared with those made by authentic VSV. For RNA analysis the supernatant fluids harvested from primary transfections were amplified once in BHK21 cells in the presence of ara-c. The resultant supernatants were used to infect BHK21 cells which were exposed to [$^3$H]uridine in the presence of actinomycin-D from 3 to 6 hours post infection. Cytoplasmic extracts were prepared, RNAs were harvested, resolved by electrophoresis on 1.75% agarose-urea gels, and detected by fluorography. RNAs that comigrated with authentic VSV genomic RNA and the five mRNAs were synthesized following infection with samples harvested from transfections that received pVSV1(+) and three support plasmids, N, P and L. No VSV RNAs were detected following passage of supernatants from transfections that did not receive both pVSV1 (+) and the support plasmids.

Viral protein synthesis was monitored following the infection of BHK21 cells at an MOI of 5. Cells were starved for methionine for 30 minutes prior to incorporation of [$^{35}$S] methionine from 1 hour post-infection for 5 hours. Cytoplasmic extracts were prepared and proteins were analyzed on a 10% polyacrylamide-SDS gel. Virus recovered from transfections of pVSV1 (+) displayed a protein profile that closely resembled those of the San Juan and Orsay strains of VSV Indiana. Furthermore, the proteins that were specifically immunoprecipitated by a VSV specific antiserum (which reacts poorly with the VSV M and P proteins) were similar in the three cases, providing further evidence that the recovered virus was VSV. However there were minor differences in the mobility of the proteins from the recovered virus, M protein providing the clearest example. These different mobilities were characteristic of the proteins encoded by the support plasmids that had been used to construct pVSV1(+), and thus provided evidence that the genome of the recovered virus was derived from the cDNA clone.

VSV recovered from the cDNA clone Contained Characteristic Sequence Markers

During the construction of pVSV1 (+) several nucleotide sequence markers were introduced with the 5' terminal 516 nucleotides which originated from the cDNA clone of DI-T RNA (Pattnaik, A. K. et al. (1992) *Cell* 69, 1011–1020). To examine the nucleotide sequence of the 5' end of the genome of the recovered virus; RT-PCR was performed. RNA was purified from the recovered virus after 3 passages, and the region from nucleotide 11026 to the extreme 5' end of the genome (nucleotide 11161) was amplified, cloned and sequenced. In comparison to the published Indiana San Juan virus sequence the following nucleotide differences were noted; nucleotides G11038A, A11070C, and an insertion of an A residue at nucleotide 11140. These results revealed that the nucleotide sequence of this region of the genome of the recovered virus was identical to the cDNA clone, and hence that the recovered virus originated from pVSV1(+).

Genome Length Negative-Sense RNA Transcripts of VSV were not Synthesized efficiently by Bacteriophage T7 RNA Polymerase.

In marked contrast to our success in recovering infectious VSV from pVSV1(+), attempts to generate infectious virus from negative-sense RNA transcripts were uniformly unsuccessful (Table 3). This was surprising, because success with negative-sense T7 transcripts of DI-T RNA (Pattnaik, A. K. et al. (1992) *Cell* 69, 1011–1020; Pattnaik, A. K. et al. (1995) *Virology* 206, 760–764) and with several subgenomic replicons (Wertz, G. W. et al. (1994) *Proc. Natl. Acad. Scie. USA* 91, 8587–8591) had suggested no inherent problems with this strategy. We therefore compared the ability of T7 RNA polymerase to synthesize genome length positive and negative-sense transcripts of VSV in vitro. pVSV(+) and pVSV1 (−) were linearized at the unique NheI site and transcribed in vitro by T7 RNA polymerase in the presence of [$^3$H]UTP. The products were analyzed on 1% agarose-urea gels, and detected by fluorography. Whereas transcripts of pVSV1 (+) were predominantly genome length, the majority of T7 transcripts of pVSV1(−) were clearly smaller than the VSV RNA. Clearly this apparent inability of T7 RNA polymerase to synthesize full length negative-sense transcripts of VSV RNA could explain the lack of infectivity of pVSV1(−).

The natural signal for transcriptional termination by T7 RNA polymerase is a strong hairpin structure followed by 6 U residues in the nascent RNA (Rosenberg, A. H. et al. (1987) *Gene* 56, 125–135). A run of 7 U residues exists at each of the intergenic junctions in the negative-strand of VSV RNA, and among the transcription products from pVSV1 (−) were four discrete RNAs of the appropriate size to represent the products of termination at the intergenic junctions. The behavior of T7 RNA polymerase when transcribing a VSV intergenic junction in the negative-sense, as compared with the positive-sense was investigated. The NP intergenic region was cloned in both the positive and negative orientation into transcription plasmids between the T7 promoter and the HDV ribozyme/T7 terminator cassettes. In vitro transcriptions were performed on each of these circular plasmids in the presence of [$^3$H]UTP and the RNA products were analyzed on a 1 % agarose-urea gel and detected by fluorography. Plasmid 8(+)NP, which generated positive-sense transcripts of the NP intergenic junction, gave the expected two RNAs that resulted form transcriptional termination at the T7 termination signal and the subsequent ribozyme mediated self cleavage to generate authentic VSV 3' termini. The smaller (200 nucleotides) product of self cleavage had run off this gel. In contrast the two plasmids 8(−)NP and 8(+)PN, that were designed to generate negative-sense transcripts of the NP intergenic junction, each yielded a major smaller RNA product in addition to the expected products of T7 termination and self-cleavage. The sizes of these smaller RNAs were consistent with termination at or very close to the NP intergenic junction, as shown by comparison with the size of the RNA made by run-off transcription from plasmid 8(+)PN linearized at the EcoRV site which is 7 nucleotides from the NP intergenic junction. These analyses show that T7 RNA polymerase terminated near the VSV NP intergenic junction when synthesizing a negative-sense RNA, but not when generating a positive-sense RNA transcript. Furthermore, the RNA products directed by pVSV1(−) suggest that similar termination occurred to a greater or lesser extent at the other intergenic junctions. The cumulative effect of this incomplete transcriptional termination by T7 RNA polymerase, at each intergenic junction in the negative-sense transcript, probably accounts for the difference in the RNAs transcribed in vitro from pVSV1(−) and pVSV1(+).

EQUIVALENTS

Those skilled in the art will recognize, or be able to ascertain using no more than routine experimentation, many equivalents of the specific embodiments of the invention described herein. Such equivalents are intended to be encompassed by the following claims.

---

We claim:

1. A pure, recombinant, replicating and spreading non-segmented RNA virus particle, comprising: 1) a functional non-segmented RNA dependent RNA polymerase (L); 2) a non-segmented virus phosphoprotein (P); 3) a non-segmented nucleocapsid (N); 4) non-segmented virus structural protein; 5) a 3' non-coding RNA sequence; 6) a 3' to 5' RNA coding sequence, which encodes the non-segmented L, P, N and non-segmented virus structural proteins required for assembly of budded infectious particles and includes a heterologous gene (X), wherein said heterologous gene (X) is inserted at a naturally occurring intergenic junction, and 7) a 5' non-coding RNA sequence, wherein components 1 thru 7 are from the same type of non-segmented RNA virus, and wherein the non-segmented RNA virus is selected from the group consisting of respiratory syncytial virus (RSV) vesicular stomatitus virus (VSV).

2. A virus particle of claim 1, wherein the non-segmented RNA virus is a respiratory syncytial virus.

3. A virus particle of claim 2, wherein the respiratory syncytial virus is a human respiratory syncytial virus.

4. A virus particle of claim 2, wherein the respiratory syncytial virus particle is a bovine respiratory syncytial virus.

5. A virus particle of claim 1, wherein the non-segmented RNA virus is vesicular stomatitus virus (VSV).

6. A pure, recombinant, replicating and non-spreading non-segmented RNA virus particle, comprising: 1) a functional non-segmented virus RNA dependent RNA polymerase (L); 2) a non-segmented virus phosphoprotein (P); 3) a non-segmented virus nucleocapsid (N); 4) non-segmented virus structural protein; 5) a 3' non-coding RNA sequence; 6) a 3' to 5' RNA coding sequence, which encodes said non-segmented virus L, P, N, but no non-segmented virus structural proteins required for assembly of budded infectious particles and includes a heterologous gene (X), wherein said heterologous gene (X) is inserted at a naturally occurring intergenic junction, and 7) a 5' non-coding RNA sequence, wherein components 1 thru 7 are from the same type of non-segmented RNA virus, and wherein the non-segmented RNA virus is selected from the group consisting of respiratory syncytial virus (RSV) vesicular stomatitus virus (VSV).

7. A virus particle of claim 6, wherein the non-segmented RNA virus is a respiratory syncytial virus.

8. A virus particle of claim 7, wherein the respiratory syncytial virus is a human respiratory syncytial virus.

9. A virus particle of claim 7, wherein the respiratory syncytial virus particle is a bovine respiratory syncytial virus.

10. A virus particle of claim 6, wherein the non-segmented RNA virus is vesicular stomatitis virus.

11. A pure, recombinant, non-segmented RNA virus transcribing particle, comprising: 1) a functional non-segmented virus RNA dependent RNA polymerase (L); 2) a non-segmented virus phosphoprotein (P); 3) a non-segmented virus nucleocapsid (N); 4) non-segmented virus structural protein; 5) a 3' non-coding RNA sequence; 6) a 3' to 5' RNA coding region, which contains an appropriate transcription initiation sequence and a heterologous gene (X), wherein said heterologous gene (X) is inserted at a naturally occurring intergenic junction and 7) a 5' non-coding RNA sequence, wherein components 1 thru 7 are from the same type of segmented RNA virus, and wherein the non-segmented RNA virus is selected from the group sting of respiratory syncytial virus (RSV) vesicular stomatitus virus (VSV).

12. A virus particle of claim 11, wherein the non-segmented virus is a respiratory syncytial virus.

13. A virus particle of claim 12, wherein the respiratory syncytial virus particle is a bovine respiratory syncytial virus.

14. A virus particle of claim 13, wherein the non-segmented virus is a rhabdovirus.

15. A virus particle of claim 11, wherein the non-segmented RNA s is vesicular stomatitis virus.

* * * * *

UNITED STATES PATENT AND TRADEMARK OFFICE
CERTIFICATE OF CORRECTION

PATENT NO. : 5,789,229
DATED : August 4, 1998
INVENTOR(S) : Gail W. Wertz, Qingzhong Yu, Laurence A. Ball, John N. Barr, and Sean P.J. Whelan It is certified that error appears in the above-identified patent and that said Letters Patent is hereby corrected as shown below:

Title page,
The title should read -- Gene Therapy Vectors and Vaccines Based on Non-Segmented Negative Stranded RNA Viruses --.

Column 41,
Line 50, "stomatitus" should read -- stomatitis --.
Line 59, "stomatitus" should read -- stomatitis --.

Column 42,
Line 41, "stomatitus" should read -- stomatitis --.
Line 62, "segmented" should read -- nonsegmented --
Line 63, "sting" should read -- consisting --.
Line 64, "stomatitus" should read -- stomatitis --.

Signed and Sealed this

Sixteenth Day of October, 2001

Attest:

NICHOLAS P. GODICI
Attesting Officer    Acting Director of the United States Patent and Trademark Office